US011077299B2

(12) United States Patent
Fuhs et al.

(10) Patent No.: US 11,077,299 B2
(45) Date of Patent: *Aug. 3, 2021

(54) IMPLANTATION OF AN ACTIVE MEDICAL DEVICE

(71) Applicant: CARDIAC PACEMAKERS, INC., St. Paul, MN (US)

(72) Inventors: Christopher Alan Fuhs, Roseville, MN (US); Andrew L. De Kock, Ham Lake, MN (US); G. Shantanu Reddy, Minneapolis, MN (US); Peter Hall, Andover, MN (US); James K. Cawthra, Jr., Ramsey, MN (US); Daniel J. Foster, Lino Lakes, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 454 days.

This patent is subject to a terminal disclaimer.

(21) Appl. No.: 15/913,369

(22) Filed: Mar. 6, 2018

(65) Prior Publication Data

US 2018/0256890 A1    Sep. 13, 2018

Related U.S. Application Data

(60) Provisional application No. 62/468,102, filed on Mar. 7, 2017.

(51) Int. Cl.
| | | |
|---|---|---|
| *A61B 17/34* | (2006.01) | |
| *A61N 1/05* | (2006.01) | |
| *A61M 25/06* | (2006.01) | |

(52) U.S. Cl.
CPC .......... *A61N 1/056* (2013.01); *A61B 17/3468* (2013.01); *A61M 25/0662* (2013.01); *A61N 2001/0578* (2013.01)

(58) Field of Classification Search
CPC .......... A61N 2001/0578; A61N 1/056; A61M 25/0662; A61B 17/3468
See application file for complete search history.

(56) References Cited

U.S. PATENT DOCUMENTS

| | | |
|---|---|---|
| 5,331,966 A | 7/1994 | Bennett et al. |
| 6,647,292 B1 | 11/2003 | Bardy et al. |

(Continued)

FOREIGN PATENT DOCUMENTS

| | | |
|---|---|---|
| WO | 2016148928 A1 | 9/2016 |
| WO | 2016149262 A1 | 9/2016 |

OTHER PUBLICATIONS

Advisory Action Before the Filing of an Appeal Brief for Application No. 15667167, dated Mar. 21, 2019.

(Continued)

*Primary Examiner* — Julie A Szpira
(74) *Attorney, Agent, or Firm* — Seager, Tufte & Wickhem LLP

(57) ABSTRACT

Implantation of a cardiac stimulus system using the ITV. Superior, intercostal, and inferior access methods are discussed and disclosed. Superior access may be performed using the brachiocephalic vein to access the ITV, with access to the brachiocephalic vein achieved using subclavian vein, using standard visualization techniques. A positioning mechanism may be advanced to the ITV, a location of the positioning mechanism may then be obtained, and an external access may then be established. Inferior external access may be accomplished inferior to the lower rib margin via the superior epigastric or musculophrenic vein. Intercostal external access may be accomplished via an intercostal vein between two ribs. A lead may then be attached to the positioning mechanism and drawn into the ITV.

18 Claims, 19 Drawing Sheets

(56) References Cited

U.S. PATENT DOCUMENTS

| | | | |
|---|---|---|---|
| 6,721,597 B1 | 4/2004 | Bardy et al. | |
| 7,149,575 B2 | 12/2006 | Ostroff et al. | |
| 7,655,014 B2 | 2/2010 | Ko et al. | |
| 7,783,340 B2 | 8/2010 | Sanghera et al. | |
| 7,818,068 B2 | 10/2010 | Meadows et al. | |
| 7,962,222 B2 | 6/2011 | He et al. | |
| 8,005,543 B2 | 8/2011 | Libbus et al. | |
| 8,157,813 B2 | 4/2012 | Ko et al. | |
| 8,311,633 B2 * | 11/2012 | Ransbury | A61F 2/95 607/36 |
| 8,386,048 B2 | 2/2013 | McClure et al. | |
| 8,433,412 B1 * | 4/2013 | Westlund | A61N 1/056 607/42 |
| 8,483,843 B2 | 7/2013 | Sanghera et al. | |
| 8,543,216 B2 | 9/2013 | Carbunaru et al. | |
| 2005/0043765 A1 * | 2/2005 | Williams | A61N 1/057 607/9 |
| 2008/0071339 A1 * | 3/2008 | Stalker | A61B 5/0215 607/119 |
| 2009/0036947 A1 * | 2/2009 | Westlund | A61N 1/3611 607/42 |
| 2011/0077726 A1 * | 3/2011 | Westlund | A61N 1/0558 607/127 |
| 2011/0190697 A1 * | 8/2011 | Farnan | A61M 25/0662 604/99.01 |
| 2011/0238078 A1 * | 9/2011 | Goode | A61B 17/30 606/129 |
| 2012/0029335 A1 * | 2/2012 | Sudam | A61N 1/05 600/374 |
| 2012/0035711 A1 * | 2/2012 | Gross | A61N 1/0514 623/1.18 |
| 2014/0200640 A1 * | 7/2014 | Wulfman | B23K 31/02 607/116 |
| 2015/0025612 A1 | 1/2015 | Haasl et al. | |
| 2015/0051610 A1 | 2/2015 | Schmidt et al. | |
| 2015/0196756 A1 | 7/2015 | Stahmann et al. | |
| 2015/0196757 A1 | 7/2015 | Stahmann et al. | |
| 2015/0196758 A1 | 7/2015 | Stahmann et al. | |
| 2015/0196769 A1 | 7/2015 | Stahmann et al. | |
| 2015/0224320 A1 | 8/2015 | Stahmann | |
| 2015/0297902 A1 | 10/2015 | Stahmann et al. | |
| 2015/0360036 A1 | 12/2015 | Kane et al. | |
| 2016/0038742 A1 | 2/2016 | Stahmann et al. | |
| 2016/0059007 A1 | 3/2016 | Koop | |
| 2016/0059022 A1 | 3/2016 | Stahmann et al. | |
| 2016/0059024 A1 | 3/2016 | Stahmann et al. | |
| 2016/0059025 A1 | 3/2016 | Stahmann et al. | |
| 2016/0089539 A1 | 3/2016 | Gilkerson et al. | |
| 2016/0151056 A1 * | 6/2016 | Lederman | A61B 17/12181 606/185 |
| 2016/0184580 A1 * | 6/2016 | Grace | A61B 17/32056 607/119 |
| 2016/0228712 A1 | 8/2016 | Koop | |
| 2016/0256692 A1 | 9/2016 | Baru | |
| 2017/0021159 A1 | 1/2017 | Reddy et al. | |
| 2017/0112399 A1 | 4/2017 | Brisben et al. | |
| 2017/0113040 A1 | 4/2017 | Brisben et al. | |
| 2017/0113050 A1 | 4/2017 | Brisben et al. | |
| 2017/0113053 A1 | 4/2017 | Brisben et al. | |
| 2018/0036527 A1 | 2/2018 | Reddy et al. | |
| 2018/0036547 A1 | 2/2018 | Reddy | |
| 2018/0133462 A1 | 5/2018 | Reddy | |
| 2018/0133463 A1 | 5/2018 | Reddy | |
| 2018/0133494 A1 | 5/2018 | Reddy | |
| 2018/0169384 A1 | 6/2018 | Reddy et al. | |
| 2018/0169425 A1 | 6/2018 | Reddy et al. | |
| 2018/0178018 A1 | 6/2018 | Reddy et al. | |
| 2018/0178019 A1 | 6/2018 | Reddy et al. | |
| 2018/0193060 A1 | 7/2018 | Reddy et al. | |
| 2018/0214686 A1 | 8/2018 | De Kock et al. | |
| 2018/0256890 A1 | 9/2018 | Fuhs et al. | |
| 2018/0264270 A1 | 9/2018 | Koop et al. | |
| 2018/0296824 A1 | 10/2018 | De Krock et al. | |
| 2018/0325480 A1 | 11/2018 | Liu et al. | |
| 2018/0344200 A1 | 11/2018 | Thakur et al. | |
| 2018/0344252 A1 | 11/2018 | An et al. | |

OTHER PUBLICATIONS

Final Office Action for U.S. Appl. No. 15/667,167, dated Jan. 10, 2019.
Non-Final Office Action for U.S. Appl. No. 15/667,167, dated Jun. 26, 2018.
Non-Final Office Action for U.S. Appl. No. 15/667,167, dated Aug. 7, 2019.
Final Office Action for U.S. Appl. No. 15/667,221, dated Apr. 11, 2019.
Non-Final Office Action for U.S. Appl. No. 15/667,221, dated Oct. 1, 2018.
Notice of Allowance and Fees Due for U.S. Appl. No. 15/667,221, dated Jul. 11, 2019.
Amendment for U.S. Appl. No. 15/667,167, dated Sep. 17, 2018.
Amendment for U.S. Appl. No. 15/667,167, dated Oct. 9, 2019.
Amendment After Final Office Action for U.S. Appl. No. 15/667,167, dated Mar. 11, 2019.
Request for Continued Examination (RCE) for U.S. Appl. No. 15/667,167, dated Apr. 10, 2019.
Amendment for U.S. Appl. No. 15/667,221, dated Dec. 21, 2018.
Amendment After Final Office Action for U.S. Appl. No. 15/667,221, dated May 22, 2019.
Moeinipour et al., "A Rare Central Venous Catheter Malposition: A Case Report," Anesth Pain Med., 4(1): 1-3, Feb. 5, 2014.
Schuder et al., "Experimental Ventricular Defibrillation with an Automatic and Completely Implanted System," Trans. Amer. Soc. Artif. Int. Organs, XVI: 207-212, 1970.
Schuder et al., "The Role of an Engineering Oriented Medical Research Group in Developing Improved Methods and Devices for Achieving Ventricular Defibrillation: The University of Missouri Experience," PACE, 16: 95-124, Jan. 1993.
Ghosh et al., "A Rare Malposition of the Thoracic Venous Catheter Introduced via the Left Internal Jugular Vein," Indian J. Crit. Care Med., 12(4): 201-203, Oct.-Dec. 2008.
Loukas et al., "The Clinical Anatomy of the Internal Thoracic Veins," Folia Morphol, 66(1): 25-32, 2007.

\* cited by examiner

IMPLANTATION OF AN ACTIVE MEDICAL DEVICE

CROSS REFERENCE TO RELATED APPLICATIONS

The present application claims the benefit of and priority to U.S. Provisional Patent Application Ser. No. 62/468,102, filed Mar. 7, 2017, titled IMPLANTATION OF AN ACTIVE MEDICAL DEVICE, the disclosure of which is incorporated herein by reference.

BACKGROUND

The implantable defibrillator has been demonstrated to extend patient lives by treatment of potentially deadly arrhythmias. Over time, various efforts have been made to address complications associated with implantation of such devices. For example, early devices generally used epicardial patch electrodes implanted via thoracotomy, with attendant surgical morbidity and significant risks of failure of the epicardial patch electrodes and associated leads. The introduction of transvenous leads represented a major advance, avoiding the thoracotomy and improving reliability. However, lead failure remained a significant issue, as the lead attachment in the heart cause the lead to flex with each heartbeat. The advent of subcutaneous defibrillators allows avoidance of these lead failure issues, with leads implanted beneath the skin and over the ribcage of the patient which are not subjected to the repeated flexing of the heart.

However, subcutaneous defibrillators require higher energy for defibrillation, causing the pulse generators for such systems to be larger than their transvenous predecessors. Both bradycardia pacing and anti-tachycardia pacing are of limited utility as such pacing subcutaneously can be very uncomfortable for the patient. This has led to interest in further alternative locations for implantable defibrillators and/or pacemakers. With such interest there is a need for new and alternative delivery methods and designs for implantable defibrillators, pacemakers, and other medical devices.

OVERVIEW

The present inventors have recognized, among other things, that the internal thoracic vasculature including, in particular, the internal thoracic vein (ITV), sometimes also referred to as the internal mammary vein, presents an opportunity for an additional alternative implant location. A positioning mechanism may be used to access the ITV using superior, intercostal, and/or inferior access methods. The location of the positioning mechanism may then be obtained and an external access may be established. A lead may then be attached to the positioning mechanism and drawn into the ITV.

A first non-limiting example takes the form of a method of implanting a lead for use in a cardiac stimulus system in a patient, the method comprising establishing access to a brachiocephalic vein of the patient, advancing a positioning mechanism from the brachiocephalic vein to and into an internal thoracic vein (ITV), wherein the positioning mechanism has a proximal end and a distal end, and the advancing step comprises advancing the distal end of the positioning mechanism into the ITV, obtaining a location of the positioning mechanism in the ITV, establishing an external access to the positioning mechanism at a position either in the ITV, the musculophrenic vein, or in the superior epigastric vein, attaching the lead to the positioning mechanism, and drawing the lead into the ITV by pulling on the positioning mechanism.

Additionally or alternatively a second non-limiting example takes the form of a method as in the first non-limiting example wherein the lead has a proximal end configured for attachment to an implantable pulse generator, and a distal end having one or more electrodes associated therewith; the step of attaching the lead to the positioning mechanism comprises attaching the distal end of the lead to the distal end of the positioning mechanism, and the step of drawing the lead into the ITV is performed by pulling on the proximal end of the positioning mechanism.

Additionally or alternatively a third non-limiting example takes the form of a method as in the first non-limiting example wherein the lead has a proximal end configured for attachment to an implantable pulse generator, and a distal end having one or more electrodes associated therewith; the step of attaching the lead to the positioning mechanism comprises attaching the proximal end of the lead to the proximal end of the positioning mechanism, and the step of drawing the lead into the ITV is performed by pulling on the distal end of the positioning mechanism at the location of the external access.

Additionally or alternatively a fourth non-limiting example takes the form of a method as in the first non-limiting example wherein the positioning mechanism is a guidewire.

Additionally or alternatively a fifth non-limiting example takes the form of a method as in the first non-limiting example wherein the distal end of the positioning mechanism has a shape controllable from the proximal end of the positioning mechanism.

Additionally or alternatively a sixth non-limiting example takes the form of a method as in the first non-limiting example wherein the distal end of the positioning mechanism includes an eyelet or suture hole.

Additionally or alternatively a seventh non-limiting example takes the form of a method as in the first non-limiting example wherein the lead has a distal end having a suture hole, and attaching the lead to the positing mechanism comprises using a suture to removeably secure the suture hole of the lead to the positioning mechanism.

Additionally or alternatively an eighth non-limiting example takes the form of a method as in the first non-limiting example wherein the distal end of the positioning mechanism includes a hook.

Additionally or alternatively a ninth non-limiting example takes the form of a method as in the first non-limiting example wherein establishing access to the brachiocephalic vein comprises accessing the subclavian vein and advancing the positioning mechanism from the access to the subclavian vein to the brachiocephalic vein.

Additionally or alternatively a tenth non-limiting example takes the form of a method as in the first non-limiting example wherein the step of obtaining a location of the positioning mechanism in the ITV further comprises obtaining a visualization of the positioning mechanism.

Additionally or alternatively an eleventh non-limiting example takes the form of a method as in the tenth non-limiting example wherein the visualization is obtained by fluoroscopy.

Additionally or alternatively a twelfth non-limiting example takes the form of a method as in the tenth non-limiting example wherein the visualization is obtained by ultrasound.

Additionally or alternatively a thirteenth non-limiting example takes the form of a method as in the first non-limiting example further comprising detaching the lead from the positioning mechanism.

Additionally or alternatively a fourteenth non-limiting example takes the form of a method as in the thirteenth non-limiting example wherein the lead is detached from the positioning mechanism subcutaneously.

Additionally or alternatively a fifteenth non-limiting example takes the form of a method as in the fourteenth non-limiting example wherein the lead is detached from the positioning mechanism subcutaneously using electromagnetic (EM) energy to break a bond between the lead and the positioning mechanism.

A sixteenth non-limiting example takes the form of an implantation tool set comprising an introducer sheath, and a positioning mechanism having a proximal end and a distal end, at least one of the proximal or distal ends comprising a coupler adapted for coupling to a lead, the positioning mechanism sized and shaped to pass into a blood vessel of the patient.

Additionally or alternatively a seventeenth non-limiting example takes the form of an implantation tool as in the sixteenth non-limiting example wherein the coupler is located at the proximal end of the positioning mechanism.

Additionally or alternatively an eighteenth non-limiting example takes the form of an implantation tool as in the sixteenth non-limiting example wherein the coupler is located at the distal end of the positioning mechanism.

Additionally or alternatively a nineteenth non-limiting example takes the form of an implantation tool as in the sixteenth non-limiting example wherein the coupler comprises a screw.

Additionally or alternatively a twentieth non-limiting example takes the form of an implantation tool as in the sixteenth non-limiting example wherein the coupler comprises a suture hole.

Additionally or alternatively a twenty-first non-limiting example takes the form of an implantation tool as in the sixteenth non-limiting example wherein the coupler comprises a hook.

Additionally or alternatively a twenty-second non-limiting example takes the form of an implantation tool as in the sixteenth non-limiting example wherein the coupler is further adapted for releasing the lead in the blood vessel of the patient.

A twenty-third non-limiting example takes the form of an implantable lead configured to couple to an implantation tool set as in any of the sixteenth through twenty-second non-limiting examples, the lead comprising a lead body having a longitudinal axis extending between a proximal end and a distal end, a coupling structure located at least on one of the proximal end or distal end and adapted to mate with the coupler, and at least one electrode disposed adjacent to the distal end of the lead body.

Additionally or alternatively a twenty-fourth non-limiting example takes the form of a lead as in the twenty-third non-limiting example wherein the coupling structure is located at the proximal end of the lead.

Additionally or alternatively a twenty-fifth non-limiting example takes the form of a lead as in the twenty-third non-limiting example wherein the coupling structure is located at the distal end of the lead.

Additionally or alternatively a twenty-sixth non-limiting example takes the form of a lead as in the twenty-third non-limiting example wherein the coupling structure comprises a receiving loop.

Additionally or alternatively a twenty-seventh non-limiting example takes the form of a lead as in the twenty-third non-limiting example wherein the coupling structure comprises a tie.

Additionally or alternatively a twenty-eighth non-limiting example takes the form of a lead as in the twenty-third non-limiting example wherein the coupling structure comprises a hole.

Additionally or alternatively a twenty-ninth non-limiting example takes the form of a lead as in the twenty-third non-limiting example wherein the coupling structure is further adapted for releasing the lead in the blood vessel of the patient.

Additionally or alternatively a thirtieth non-limiting example takes the form of a lead as in the twenty-ninth non-limiting example wherein electromagnetic energy is applied to the coupling structure to release the lead from the implantation tool.

Additionally or alternatively a thirty-first non-limiting example takes the form of a lead as in the twenty-third non-limiting example wherein a first portion of the lead is configured for deployment in an ITV of the patient and a second portion is configured for deployment in an intercostal vein of the patient.

Additionally or alternatively a thirty-second non-limiting example takes the form of a lead as in the thirty-first non-limiting example wherein the at least one electrode is disposed on the first portion of the lead and a second electrode is disposed on the second portion of the lead.

Additionally or alternatively a thirty-third non-limiting example takes the form of a lead as in the twenty-third non-limiting example further comprising a connector at the proximal end of the lead configured to couple to an implantable medical device.

Additionally or alternatively a thirty-fourth non-limiting example takes the form of a lead as in the thirty-third non-limiting example wherein the connector has an adjustable shape.

Additionally or alternatively a thirty-fifth non-limiting example takes the form of a lead as in the thirty-third non-limiting example wherein the connector is sized and shaped to pass into the blood vessel of the patient.

A thirty-sixth non-limiting example takes the form of a method of implanting a lead for use in a cardiac stimulus system in a patient, the method comprising establishing access to a brachiocephalic vein of the patient, advancing a positioning mechanism from the brachiocephalic vein to and into an internal thoracic vein (ITV), wherein the positioning mechanism has a proximal end and a distal end, and the advancing step comprises advancing the distal end of the positioning mechanism into the ITV, advancing the distal end of the positioning mechanism from the ITV to and into a tributary vein of the ITV, obtaining a visualization of the positioning mechanism in at least the tributary vein of the ITV, establishing an external access to the positioning mechanism at a position in the tributary vein of the ITV, attaching the lead to the positioning mechanism, and drawing the lead into at least the ITV by pulling on the positioning mechanism.

Additionally or alternatively a thirty-seventh non-limiting example takes the form of a method as in the thirty-sixth non-limiting example wherein the lead has a proximal end configured for attachment to an implantable pulse generator, and a distal end having one or more electrodes associated therewith; the step of attaching the lead to the positioning mechanism comprises attaching the distal end of the lead to the distal end of the positioning mechanism, and the step of drawing the lead into the ITV is performed by pulling on the proximal end of the positioning mechanism.

Additionally or alternatively a thirty-eighth non-limiting example takes the form of a method as in the thirty-sixth non-limiting example wherein the lead has a proximal end configured for attachment to an implantable pulse generator, and a distal end having one or more electrodes associated therewith; the step of attaching the lead to the positioning mechanism comprises attaching the proximal end of the lead to the proximal end of the positioning mechanism, and the step of drawing the lead into the ITV is performed by pulling on the distal end of the positioning mechanism at the location of the external access.

Additionally or alternatively a thirty-ninth non-limiting example takes the form of a method as in the thirty-sixth non-limiting example wherein the positioning mechanism is a guidewire.

Additionally or alternatively a fortieth non-limiting example takes the form of a method as in the thirty-sixth non-limiting example wherein the distal end of the positioning mechanism has a shape controllable from the proximal end of the positioning mechanism.

Additionally or alternatively a forty-first non-limiting example takes the form of a method as in the thirty-sixth non-limiting example wherein the distal end of the positioning mechanism includes an eyelet or suture hole.

Additionally or alternatively a forty-second non-limiting example takes the form of a method as in the thirty-sixth non-limiting example wherein the lead has a distal end having a suture hole, and attaching the lead to the positing mechanism comprises using a suture to removeably secure the suture hole of the lead to the positioning mechanism.

Additionally or alternatively a forty-third non-limiting example takes the form of a method as in the thirty-sixth non-limiting example wherein the distal end of the positioning mechanism includes a hook.

Additionally or alternatively a forty-fourth non-limiting example takes the form of a method as in the thirty-sixth non-limiting example wherein establishing access to the brachiocephalic vein comprises accessing the subclavian vein and advancing the positioning mechanism from the access to the subclavian vein to the brachiocephalic vein.

Additionally or alternatively a forty-fifth non-limiting example takes the form of a method as in the thirty-sixth non-limiting example wherein the step of obtaining a location of the positioning mechanism in the ITV further comprises obtaining a visualization of the positioning mechanism.

Additionally or alternatively a forty-sixth non-limiting example takes the form of a method as in the forty-fifth non-limiting example wherein the visualization is obtained by fluoroscopy.

Additionally or alternatively a forty-seventh non-limiting example takes the form of a method as in the forty-fifth non-limiting example wherein the visualization is obtained by ultrasound.

Additionally or alternatively a forty-eighth non-limiting example takes the form of a method as in the thirty-sixth non-limiting example further comprising detaching the lead from the positioning mechanism.

Additionally or alternatively a forty-ninth non-limiting example takes the form of a method as in the forty-eighth non-limiting example wherein the lead is detached from the positioning mechanism subcutaneously.

Additionally or alternatively a fiftieth non-limiting example takes the form of a method as in the forty-ninth non-limiting example wherein the lead is detached from the positioning mechanism subcutaneously using electromagnetic (EM) energy to break a bond between the lead and the positioning mechanism.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
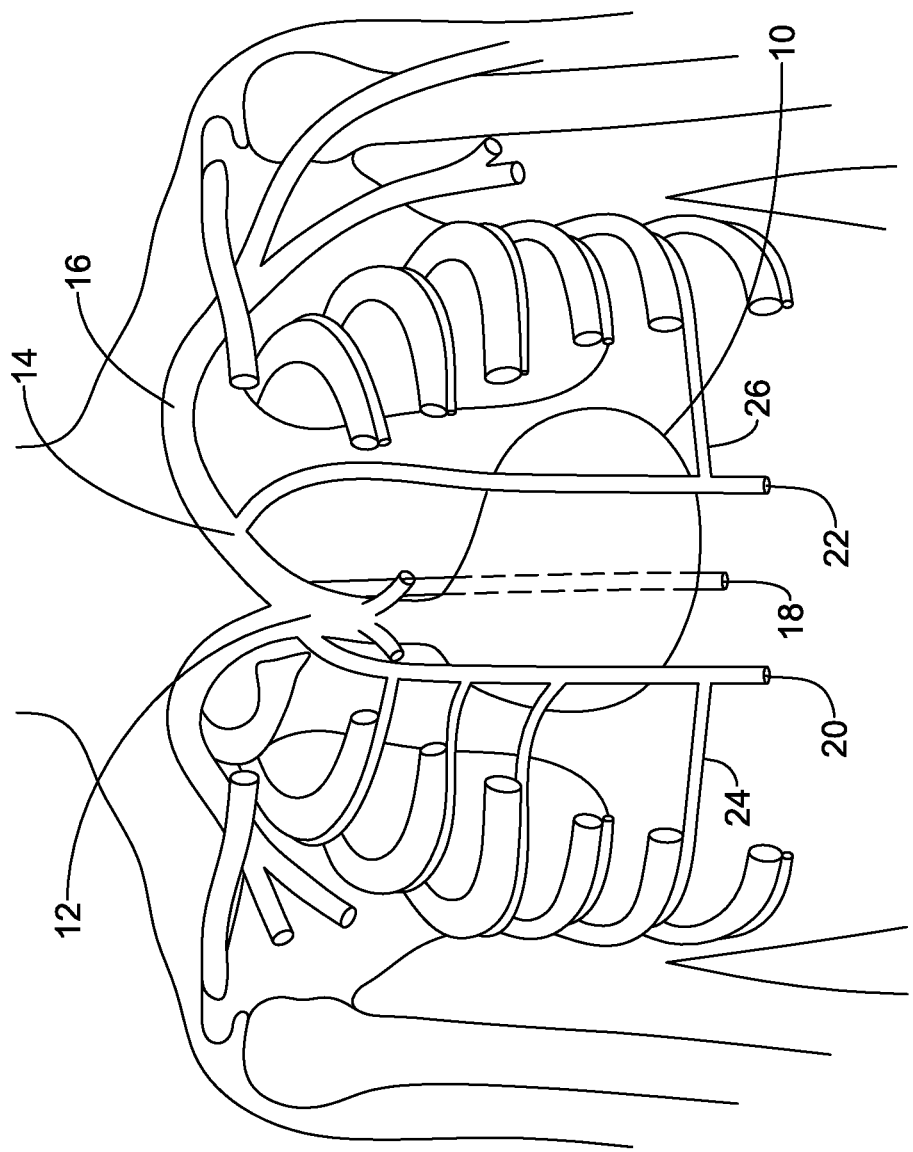
FIG. 1 illustrates the thoracic anatomy including placement of the internal thoracic veins (ITVs)

The S-ICD System from Boston Scientific provides benefits to the patient including the preservation of transvenous anatomy and avoidance of intracardiac leads, which may fracture and/or may serve as conduits for infection to reach the heart, and can occlude blood vessels going into the heart, making later placement of leads or other devices in the heart more difficult. Some examples and discussion of subcutaneous lead implantation may be found in U.S. Pat. Nos. 8,157,813, 6,721,597, and 7,149,575, as well as US PG Publication No. 20120029335 the disclosures of which are incorporated herein by reference.

While many patients can be well treated with the S-ICD System, there continue to be limitations. Increased energy requirements of the S-ICD System, perceived difficulty with providing chronic bradycardia pacing, and unavailability of anti-tachycardia pacing to terminate select fast tachycardias, have created interest in alternative defibrillator and/or pacemaker placement techniques. One proposal has included a substernal placement, with a lead extending beneath the sternum from a position inferior to the lower rib margin, such as in US PG Patent Application Pub. No. 20170021159 titled SUBSTERNAL PLACEMENT OF A PACING OR DEFIBRILLATING ELECTRODE, the disclosure of which is incorporated herein by reference. Proposals for a substernal device have been referred to as extravascular, insofar as the lead does not enter or reside in the vasculature. Such devices are distinct from early generation epicardial devices in that the lead and electrode would not touch the heart or enter or be secured to the pericardium.

The present inventors have identified still a further alternative. In human anatomy, the internal thoracic vein (ITV), which may also be referred to as the internal mammary vein, is a vessel that drains the chest wall and breasts. There are both left and right internal thoracic veins on either side of the sternum, beneath the ribs. The ITV arises from the musculophrenic and superior epigastric veins, accompanies the internal thoracic artery along its course and terminates in the brachiocephalic vein. Use of this vessel for cardiac device implantation is discussed in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference. The inventors have recognized that the ITV may make a suitable location for placement of a cardiac stimulus lead, such as the leads discussed in U.S. patent application Ser. No. 15/846,060, titled LEAD WITH INTEGRATED ELECTRODES, the disclosure of which is incorporated herein by reference and U.S. patent application Ser. No. 15/846,081, titled IMPLANTATION OF AN ACTIVE MEDICAL DEVICE USING THE INTERCOSTAL VEIN, the disclosure of which is incorporated herein by reference. While much of the following disclosure focuses on the use of the ITV, many of these concepts could also be applied to the internal thoracic arteries, which may sometimes be referenced as the internal mammary arteries.

Figure 2:
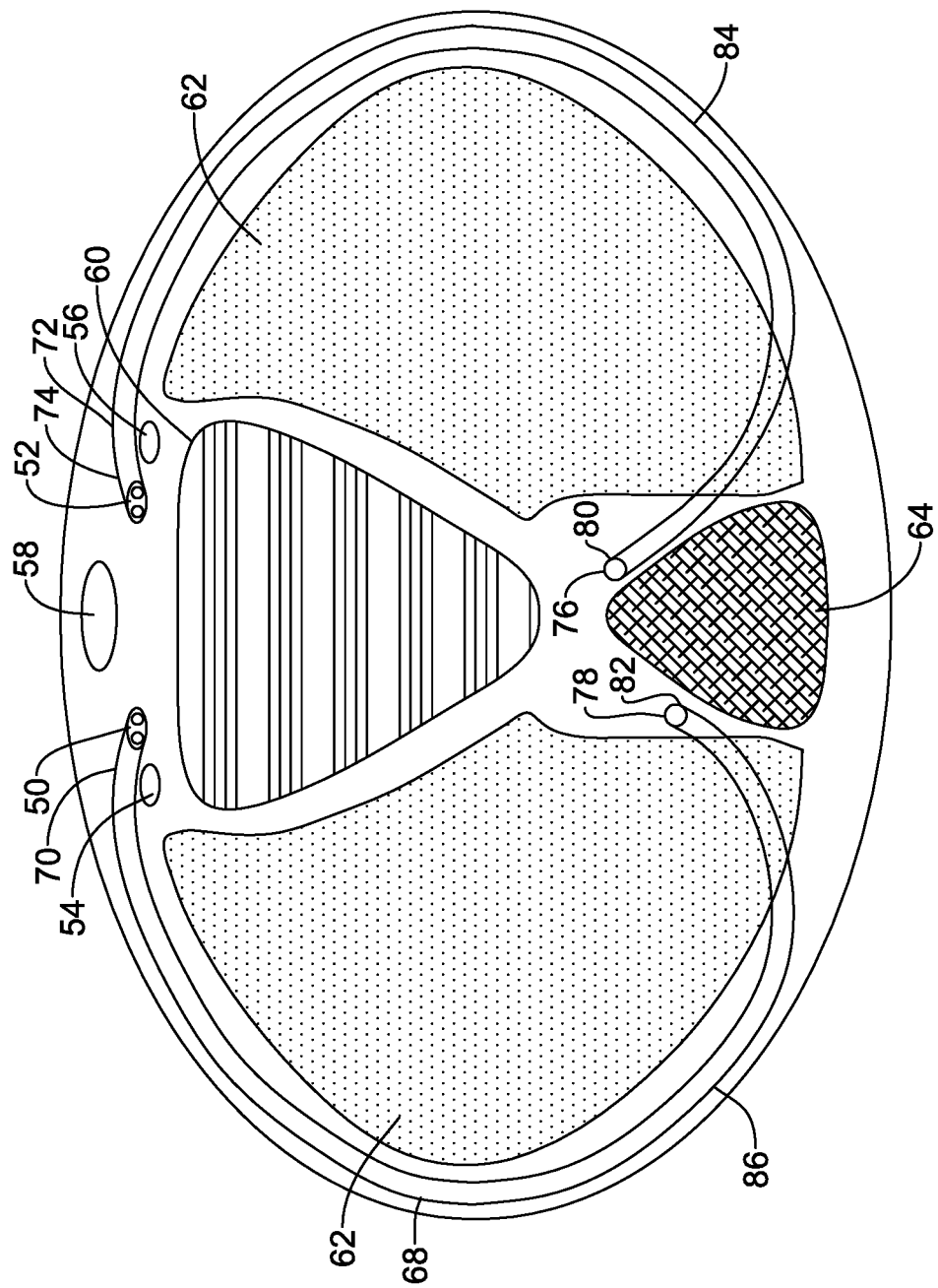
FIG. 2 shows the torso in a section view to highlight the location of the ITVs and other structures.

FIG. 1 illustrates the thoracic anatomy including location of the internal thoracic veins (ITVs) 20, 22. A right intercostal vein 24 may couple to the right ITV 20 and a left intercostal vein 26 may couple to the left ITV 22. The right and left intercostal veins 24, 26 may each run along a costal groove on an inferior portion of a rib. Additionally, an artery (not shown) and a nerve (not shown) may be located inferior (in that order) to the intercostal veins 24, 26 and also run along the costal groove. An outline of the heart is shown at 10, with the superior vena cava (SVC) shown at 12. The brachiocephalic veins 14 couple to the SVC 12 and extend past various cephalic branches (not shown) to the subclavian vein 16. The azygos vein is also shown at 18. As can be seen, the right and left ITV 20, 22 couple to the respective right and left brachiocephalic veins 12, 14. FIG. 2 shows the torso in a section view to highlight the location of various vascular structures. More particularly, in the example, the left and right ITV are shown at 50, 52, running parallel to and more central of the internal thoracic arteries 54, 56, on either side of the sternum 58. The heart is shown at 60, with the lungs at 62 and spinal column at 64. The ITV 50, 52 lie beneath the ribs but outside and separate from the pleurae of lungs 62. The ribs are omitted in the drawing in order to show the intercostal veins. A left anterior intercostal vein 68 runs along the inferior portion of a rib and couples to the left ITV 50 at junction 70, forming an ostium at the point where the left anterior intercostal vein 68 flows into the left ITV 50. Additionally, a right intercostal vein 72 runs along the inferior portion of another rib and couples to the right ITV 52 at junction 74, forming an ostium at the point where the anterior intercostal vein 72 flows into the right ITV 52.

An azygos vein and a hemiazygos vein are shown at 76, 78, running parallel to and on either side, more or less, of the spinal column 64. The azygos vein 76 and the hemiazygos vein 78 also lie beneath the ribs but outside and separate from the pleurae of lungs 62. The left posterior intercostal vein 86 couples to the hemiazygos vein 78 at a junction 82, forming an ostium at the point where the intercostal vein 68 flows into the hemiazygos vein 78. Additionally, the right posterior intercostal vein 84 couples to the azygos vein 76 at a junction 80, forming an ostium at the point where the intercostal vein 72 flows into the azygos vein 76.

Figure 3B:
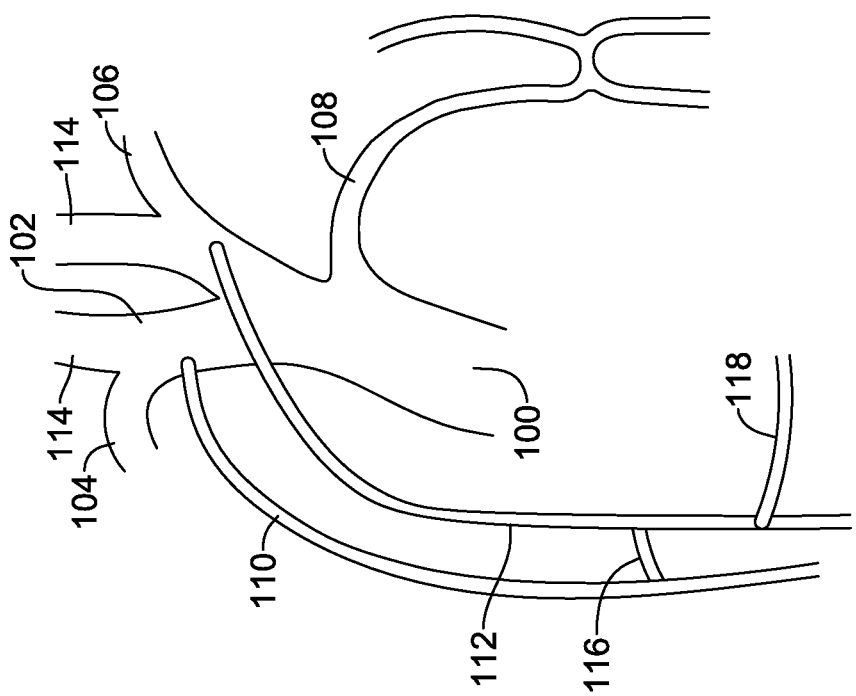
FIGS. 3A-3B show the ITVs and linked vasculature in isolation.
Figure 3A:
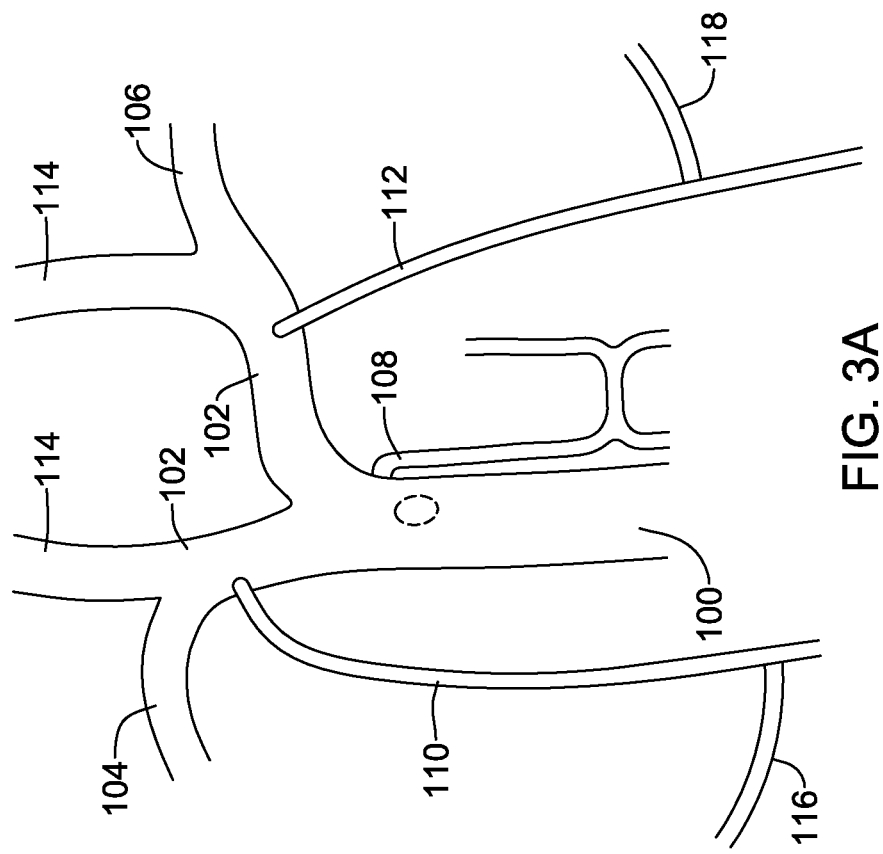

FIGS. 3A-3B show the ITV and linked vasculature in isolation. FIG. 3A is an anterior view of selected portions of the venous structure of the upper torso, and FIG. 3B is a lateral view of the same. The SVC is shown at 100, with the brachiocephalic veins 102 splitting at the upper end of the SVC. The right subclavian vein is at 104, and the left subclavian vein is at 106. The azygos vein is included in the illustration at 108, extending off the posterior of the SVC, and running inferiorly posterior of the heart as can be understood from the lateral view of FIG. 3B. The right and left ITV are shown at 110, 112. These each branch off at a location that is considered part of the brachiocephalic veins 102. Selected right and left intercostal veins are shown at 116, 118. There are left and right intercostal veins along the lower margin of each of the ribs. In several embodiments the intercostal veins of the $5^{th}$, $6^{th}$, or $7^{th}$ ribs are proposed for implantation of a lead with access through the ITV to the intercostal vein or from the intercostal vein to the ITV. In one example, the intercostal vein of the $6^{th}$ rib is used for implantation. In other examples, implantation may be more superior or inferior than these locations, as desired. These may branch off at a location of the right and left ITV's and continue to run along a coastal groove of an inferior portion of a the ribs. The internal jugular veins are also shown at 114. As shown above in FIG. 2, the intercostal veins 116, 118 wrap around to the azygos, hemiazygos or accessory hemiazygos veins, depending on which of left or right, and how superior or inferior the intercostal vein 116, 118 is. In some examples, an intercostal vein 116, 118 may be used to access the posterior of the patient for implant on the back of the patient of a lead for sensing or therapy delivery, or even to access still further the azygos, hemiazygos, or accessory hemiazygos veins, if desired, for implantation of a lead, electrode, or device.

FIGS. 4A-4F show access to and implantation of a lead in the ITV 158. Starting with FIG. 4A, the heart is shown at 150 with the SVC at 152 and the brachiocephalic vein right branch at 154 and left branch at 156. Access to the subclavian vein 160 is shown at 170 using standard access techniques known in the art for implanting traditional transvenous pacemakers and defibrillators. For example, the Seldinger technique may be used by creating a puncture with a hollow needle or trocar, for example under ultrasound guidance, introducing a positioning mechanism (e.g., a guidewire) through the needle, removing the needle, and then inserting an introducer sheath 172, which may have a valve at its proximal end, over the positioning mechanism. Other venipuncture or cutdown techniques may be used instead. Other vessels may be accessed instead of the subclavian vein using similar techniques including, for example, the jugular, cephalic, or axillary veins.

Into the access at 170, an introducer sheath 172 is inserted and advanced to a location to place its distal tip 180 near the ostium of the left ITV 158. Contrast injection may be useful to visualize the ITV structures and the ostia of the ITVs. A guide catheter 174 and a distal end 184 of a positioning mechanism 176 may then be introduced through the introducer sheath 172. In other examples, a shorter introducer sheath may be used, with the guide catheter 174 used to traverse the distance to the relevant ostium.

In certain embodiments, the positioning mechanism 176 may be a guidewire and may be the same as used in gaining initial access 170 (if one is used to gain access 170), or may be a different guidewire. In an example, the positioning mechanism 176 is preloaded in the guide catheter and both are introduced at the same time until the guide catheter 174 is at a desired location relative to the ostium of the selected ITV. The distal end 184 of the positioning mechanism 176, which may be deflectable or steerable, can then be used to enter the left ITV 158 through the ostium thereof, passing down into the left ITV 158. Furthermore, in various embodiments, the distal end 184 may have an adjustable shape. In some instances, the shape may be controllable from a proximal end 186 of the positioning mechanism 176. In some cases, the ability to adjust the shape of the distal end 184 may assist the positioning mechanism 176 in advancing through tight or tortuous anatomy.

The positioning mechanism 176 passing into the ITV from a superior position will need to pass through the valves of the ITV in a direction counter to their natural tendency (the valves in the veins prevent blood from flowing inferiorly). For an example where the positioning mechanism 176 passes unsupported by a guide catheter into the ITV from a superior position, the positioning mechanism 176 may be a preferably stiff guidewire. In some examples, the positioning mechanism 176 may be at least two guidewires that are used, a first more flexible and steerable guidewire to obtain initial access via the ostium of the ITV, and a second, stiffer guidewire that is sufficiently pushable to allow passage through the valves in the ITV.

In some examples, the guide catheter 174 is introduced first and the positioning mechanism 176 is introduced next. For example, a steerable or curved guide catheter 174 may traverse the introducer sheath 172 to its distal end 180 and then, using steering of the guide catheter or a precurved structure of the guide catheter, would then turn as shown at 182 to enter the left ITV 158. The positioning mechanism 176 may then be introduced through the guide catheter 174 and advanced into the left ITV 158.

Figure 4A:
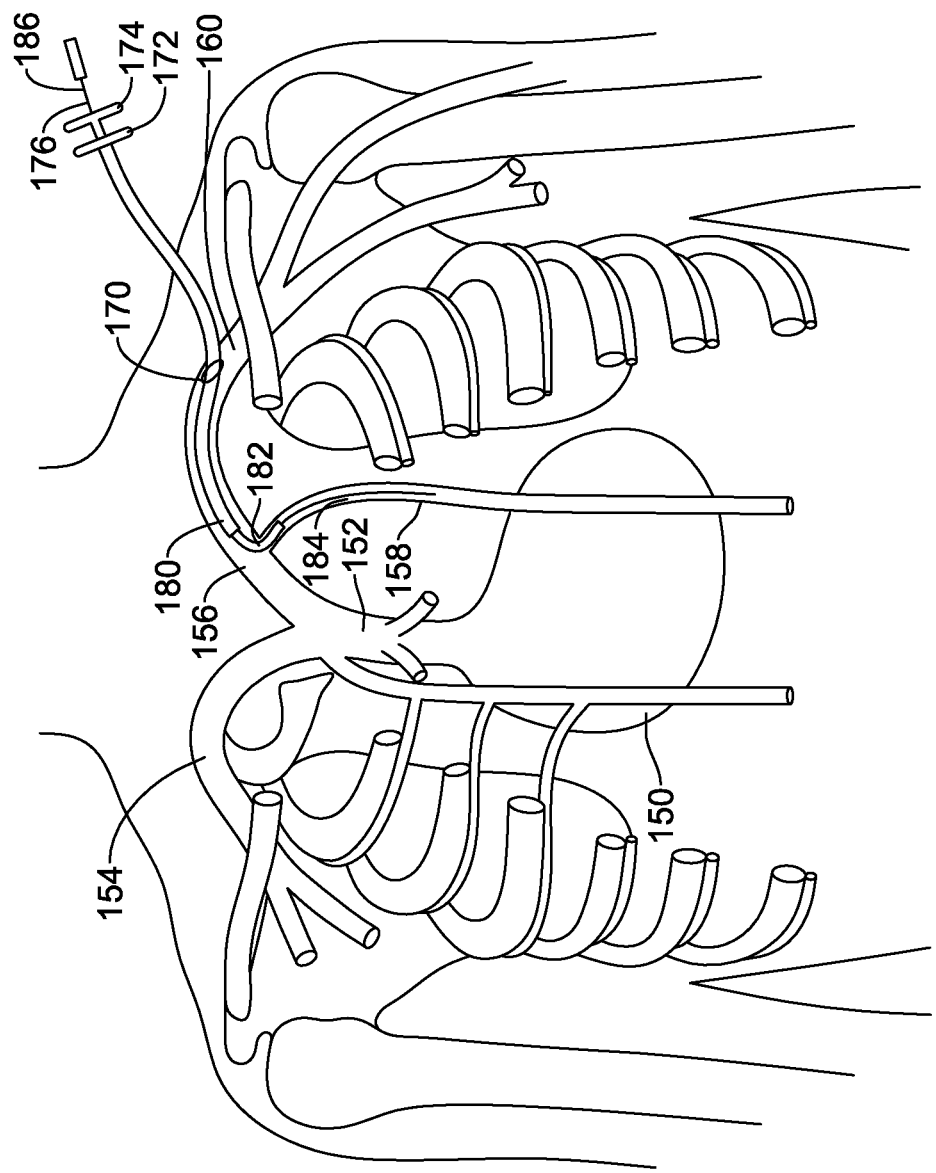
FIGS. 4A-4F show access to and implantation of a lead in the left ITV.
Figure 4B:
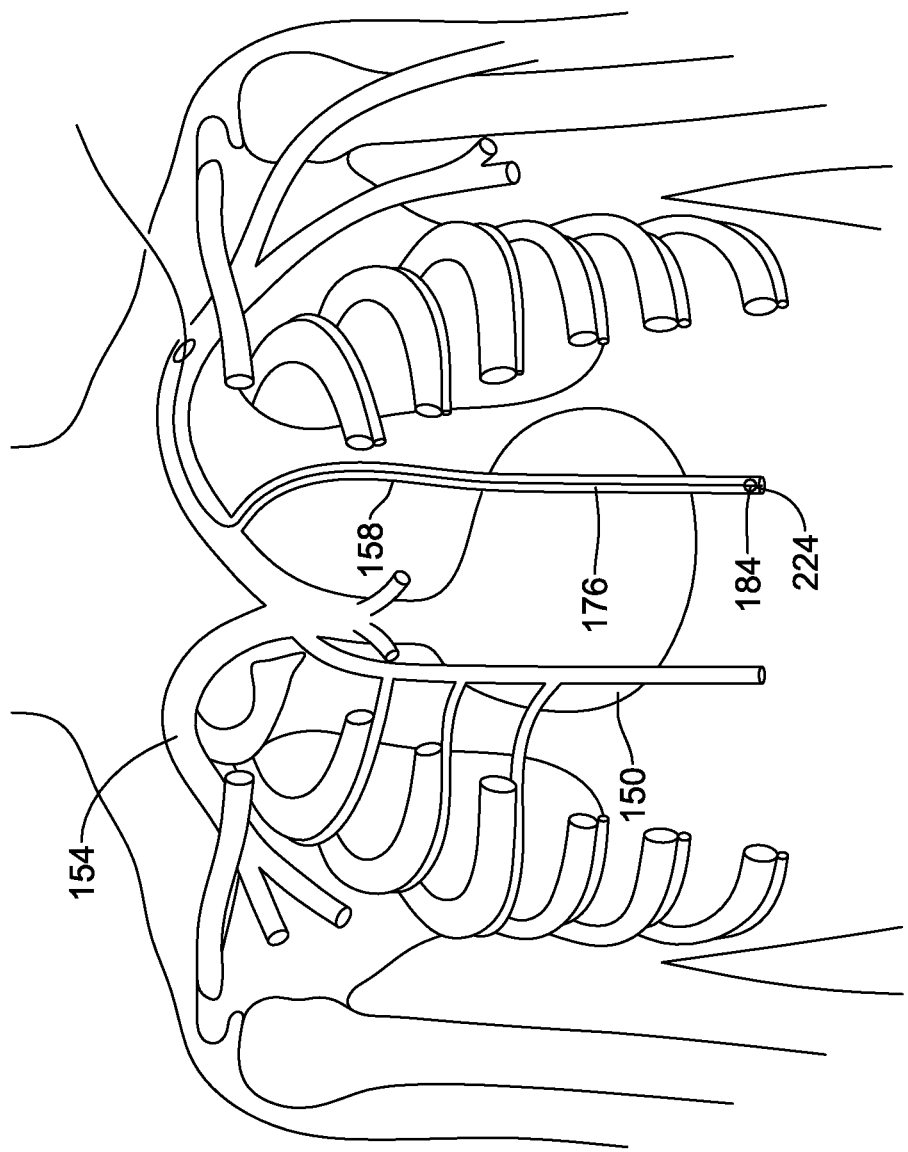

FIG. 4B shows the distal end 184 of the positioning mechanism 176 in the ITV 158. In certain cases, the ITV 158 may have a diameter on the order of 3 mm or greater and in addition to the anatomy surrounding the ITV, discussed in regard to FIGS. 1 and 2, it is also recognized that the particular body characteristics from patient to patient may vary including, for example, any venous abnormality, scarring in the area (such as related to any prior sternotomy or the like) as well as the body habitus (overweight or underweight patients). As a result, locating the ITV 158 may be difficult. In some cases, the presence of the positioning mechanism 176 inside the ITV may disclose the location of the ITV 158 and increase the accuracy of establishing an external access 224. Therefore, in various embodiments, the positioning mechanism 176 may be located.

For example, in some instances, the positioning mechanism 176 may be a radiopaque guidewire. The positioning mechanism 176 may be instead a stylet, a hypotube, or a catheter having sufficient column strength to allow pushing through blood vessels to desired position, and further with sufficient strength to allow pulling of a lead as described further below. In other cases, a radiopaque material may be placed over the positioning mechanism or a portion thereof.

When the positioning mechanism 176 is inside the ITV 158, the positioning mechanism 176 may then be visualized, for example, using x-ray or fluoroscopy. An individual (e.g., a physician) may then observe the positioning mechanism 176 and adjust the positioning mechanism 176 inside the ITV 158, if needed, to a desired location. Once the positioning mechanism 176 is at the desired location, the proper external access 224 position (e.g., near the end of the distal end of the positioning mechanism 176 inside the ITV 158 or inside the musculophrenic or superior epigastric veins) may be identified. For instance, the physician may use a fluoroscope image to identify the positioning mechanism 176 and place forceps in the view range of the fluoroscope to get a surface position of the positioning mechanism 176 and thus, establish the external access 224 position. In another embodiment, fluoroscope imaging may be used to identify the positioning mechanism 176 and an x-ray may be used to identify the xiphoid, and the external access 224 position may be based on the location of the positioning mechanism 176 and the location of the xiphoid.

In some examples, instead of an x-ray, ultrasound imaging may be used to identify the xiphoid. In some examples, fluoroscope imaging may not be used and ultrasound imaging may be used to identify the positioning mechanism 176 and the physician may use an ultrasound needle in the view range of the ultrasound to establish the position of the positioning mechanism 176 and thus, establish the external access 224 position relative to the ultrasound needle. In some cases, an element may be added to a needle that enables the needle to be picked up by an ultrasound. For instance, the needle may include an ultrasound transducer, a sealed air-filled tube, or another element having dramatic density change of which the ultrasound may be able to detect against standard body tissue. In still further embodiments, a special positioning mechanism 176 may be used that discloses its position in some shape or form in the ITV 158 that enables the physician to establish the external access 224 position. If desired, an illuminating element such as an LED may be positioned at or near the distal tip of the positioning mechanism 176 to allow ready transcutaneous visualization thereof. These are just some examples of how the positioning mechanism 176 may be used to establish the external access 224. In other embodiments, the positioning mechanism 176 may be used in conjunction with other conventional locating or visual techniques known by those skilled in the art.

Figure 5:
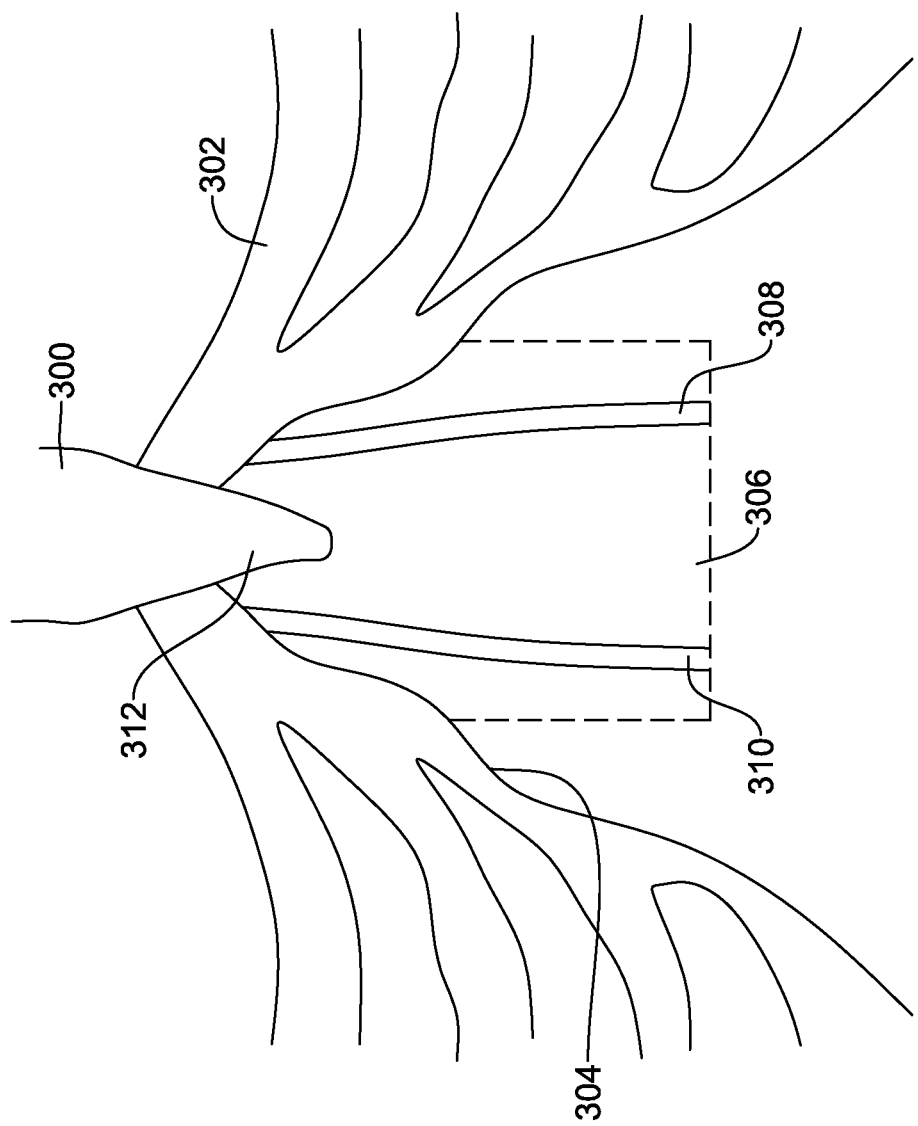
FIG. 5 shows in close view a location inferior to the lower rib margin where the ITV may be accessed inferiorly via the superior epigastric vein or musculophrenic vein.

FIG. 5 illustrates in close view of a location inferior to the lower rib margin where the superior epigastric vein may be accessed. This region may be referred to as the inferior thoracic aperture. The patient anatomy is shown in part including the sternum 300 and ribs 302, with the lower rib margin at 304. A cutout area is shown at 306 in order to illustrate the approximate location for accessing the right or left ITV using the superior epigastric veins. As used herein, the "ITV" is the name applied for the vein while it runs beneath the chest, that is, superior to the lower margin of the ribs. Inferior of this location, the blood vessel is referred to (at least in this description) as the superior epigastric vein. The left superior epigastric vein is shown at 308, and the right superior epigastric vein is shown at 310. In order to access either vein 308, 310, a physician may use the visualization of the positioning mechanism 176 to obtain external access into the desired vein 308, 310 on the desired side of the xiphoid 312.

The musculophrenic vein runs along the lower rib margin 304 and may instead, or also, be accessed in a manner similar to that of the superior epigastric vein. The musculophrenic vein and superior epigastric vein come together at the lowest end of the ITV. The musculophrenic vein may be accessed using similar methods as for the superior epigastric vein such as by ultrasound-guided Seldinger technique. Due to its adjacency to a bony structure (the costal margin), the musculophrenic vein may be useful as its access may be simpler than that of the superior epigastric vein, as the position can be readily ascertained. Further details on use of the musculophrenic vein for ITV access can be found in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference.

Figure 4C:
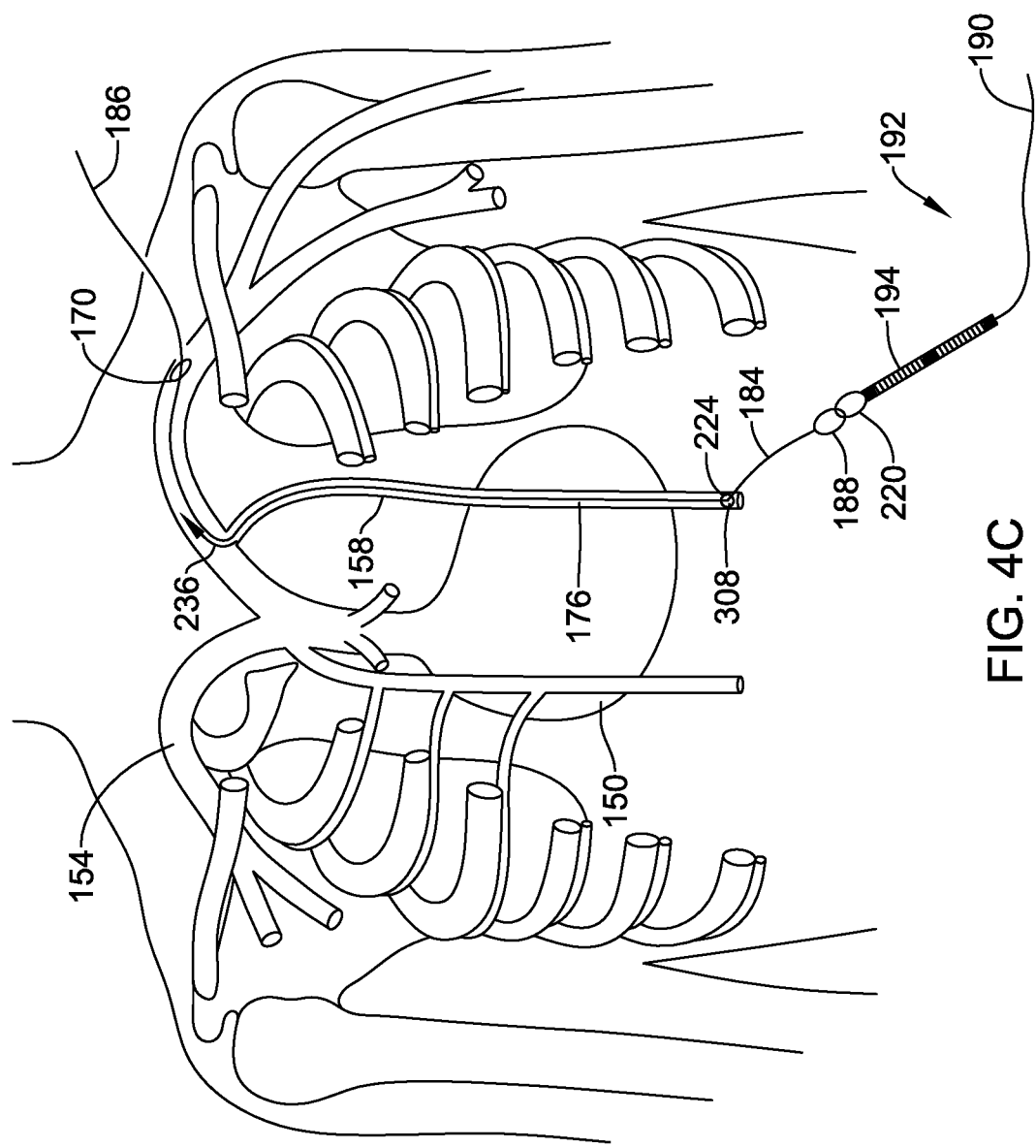

In certain embodiments, as shown in FIG. 4C, access to the distal end 184 of the positioning mechanism 176 may be obtained through the external access 224. In some cases, the distal end 184 of the positioning mechanism 176 may also include an attachment mechanism 188. Furthermore, as stated herein, the distal end 184 may have an adjustable shape. In some instances, the positioning mechanism 176 and the attachment mechanism 188 may be a formed, single-piece, and adjusting the shape of the distal end 184 means adjusting the shape of the attachment mechanism 188. As a result, the shape of the attachment mechanism 188 may change from a compressed state that may assist in advancing the positioning mechanism 176 through tight or tortuous anatomy to an expanded state that may assist the positioning mechanism 176 in attachment capabilities.

The attachment mechanism 188 may be any suitable means of fastening that may include, but is not limited to, an eyelet or a suture with a suture hole or holes, a hook, a snare, a threaded screw, pins, etc. In some cases, a distal end 194 of a lead 192 may include a compatible attachment mechanism 220 that may be configured to attach or couple to the attachment mechanism 188. The compatible attachment mechanism 220 may also include any suitable means of fastening the distal end 194 of the lead 192 to the attachment mechanism 188 of the positioning mechanism 176. For example, the compatible attachment mechanism 220 may include, an eyelet or a suture with a suture hole or holes, a hook, receiving loops, ties, pins, etc. In some cases, attaching the lead 192 to the positioning mechanism 176 may comprise using the suture on the positioning mechanism 176 to removeably secure the suture hole of the lead to the positioning mechanism 176. Various such structures are shown in U.S. Pat. No. 8,718,793 for use in coupling a subcutaneous lead to a subcutaneous electrode insertion or tunneling tool.

Once the distal end 184 of the positioning mechanism 176 is attached to the distal end 194 of the lead 192, advancement to the ITV 158 may be achieved by pulling the proximal end 186 of the positioning mechanism 176 from the access location 170, as shown by arrow 236, and drawing the lead 192 from the external access 224, into the left superior epigastric vein 308 (or alternatively the musculophrenic vein), to the ITV 158, and pulling or advancing the lead 192 to a desired level within the ITV 158. When the lead 192 is at the desired position/level, the lead 192 may be detached from the positioning mechanism 176. In some cases, an incision may be made to detach the lead 192 from the positioning mechanism 176. In some cases, the lead 192 may be detached from the positioning mechanism subcutaneously. For example, electromagnetic energy (e.g., RF energy) may be used to break the bond between the lead 192 and the positioning mechanism 176.

In one example, the lead 192 is long enough to pulled all the way to the superior access point 170 to facilitate removal of the positioning mechanism 176 while the proximal end of the lead remains outside the patient or at least outside the ITV. Once detached from the positioning mechanism 176, the lead can then be repositioned within the ITV and/or brachiocephalic vessel. A distal end of the lead may remain near the or at the superior access point 170 to provide yet another vector for sensing and/or defibrillation, if desired, or to allow anchoring thereat.

In various embodiments, before implantation, the lead 192 may have a cover (e.g., a sheath) or cap placed over it that may protect it during the implantation process. A straightening sheath or stylet may be used to hold the lead 192 in a restrained or straight configuration during initial positioning. The straightening sheath or stylet may then be removed to allow the lead 192 to anchor itself in a desired position once in place using, for example, a helical, curved, or pigtail shape.

Figure 4D:
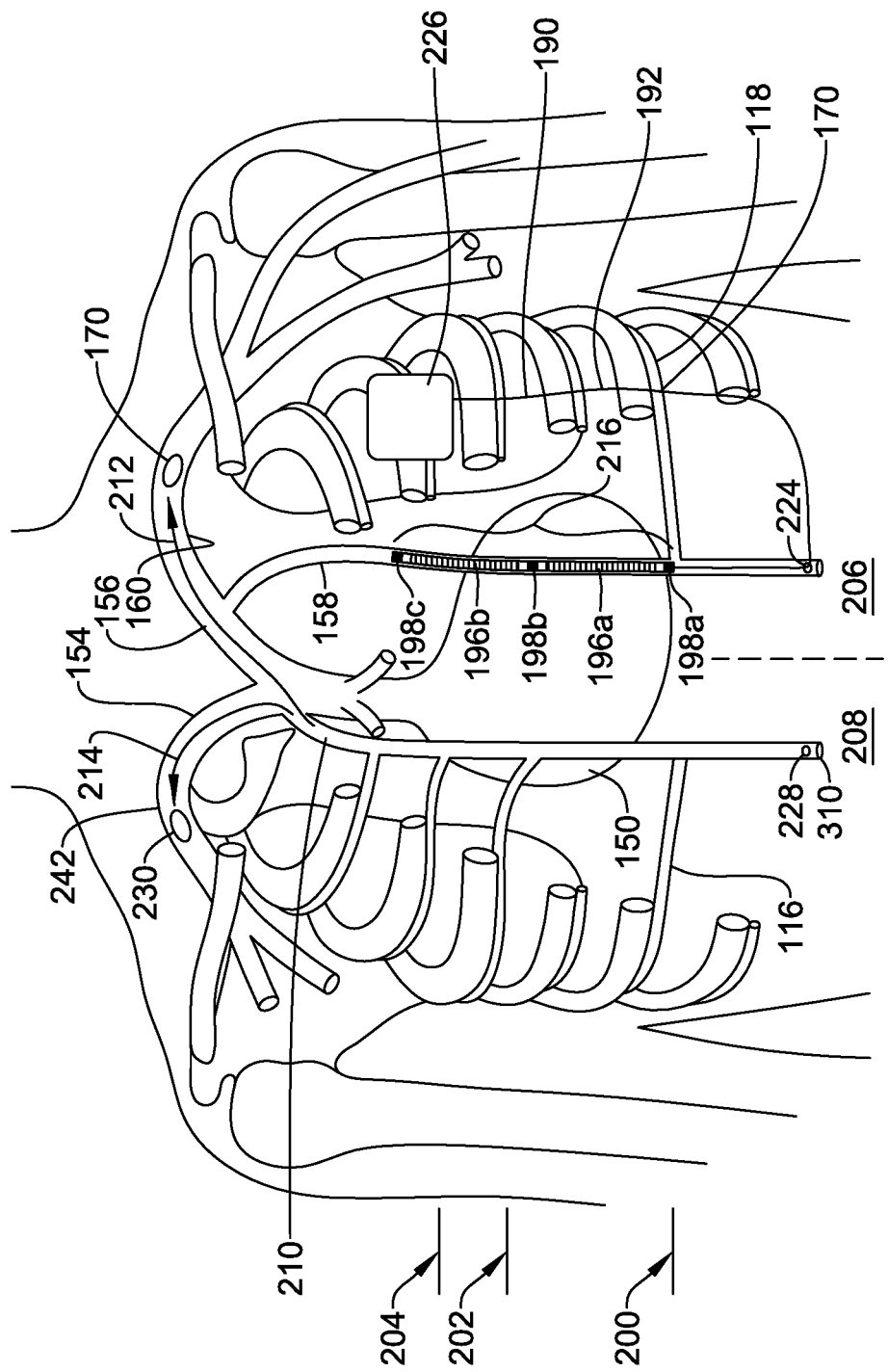

FIG. 4D shows implantation of an implantable cardiac stimulus system. The system includes an implantable pulse generator 226 which may be placed in the subclavicular location shown (or any other suitable position, as desired). In some cases the implantable pulse generator 226 may be placed at the high-pectoral or traditional transvenous position. In some cases, the implantable pulse generator 226 may be placed at approximately the left axilla. For example, the implantable pulse generator 226 may be placed at the anterior axillary line, the midaxillary line, or in the posterior axillary line. The implantable pulse generator 226 may also be placed still more posterior beneath the lattisimus dorsi, using a reported method in Kondo et al., "Successful Intermuscular Implantation Of Subcutaneous Implantable Cardioverter Defibrillator In A Japanese Patient With Pectus Excavatum." Journal of Arrhythmia, 2016, 10.1016.

According to various embodiments, the lead 192 may have a proximal end 190 configured to extend from the ITV 158 or the musculophrenic or superior epigastric veins and attach to the implantable pulse generator 226. Moreover, the distal end 194 of the lead 192 may include one or more electrodes. In the example shown in FIG. 4D, the lead 192 includes a multi-electrode distal end structure 216. The structure 216 includes a proximal coil 196A separate from a distal coil 196B. The coils 196A/B and canister 226 may serve as therapy delivery electrodes. As such there may be multiple therapy vectors such as between coil 196A and coil 196B, between either of coils 196A and 196B and the canister 226, or between a combination of two of the three therapy electrodes 196A, 196B and canister 226, and the third such electrode, such as by linking coils 196A and 196B in common as the anode or cathode relative to the canister 226.

A plurality of ring electrodes may be provided as shown at 198A, 198B, and 198C. Electrode 198C may also or instead be a tip electrode. Electrodes 198A/B/C may serve as sensing electrodes. The coils 196A, 196B may also serve as sensing electrodes. These various electrodes may be used for sensing cardiac signals in various combinations using, for example, methods and circuitry discussed in U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH, and U.S. Pat. No. 8,483,843, SENSING VECTOR SELECTION IN A CARDIAC STIMULUS DEVICE WITH POSTURAL ASSESSMENT, and/or US PG Patent Application Pub. Nos. 20170112399, 20170113040, 20170113050, and 20170113053, the disclosures of which are incorporated herein by reference.

In addition, one or more of the ring or tip electrodes 198A, 198B, 198C may be used for therapy delivery. In an example, defibrillation therapy may use coils 196A, 196B coupled in common as the opposing pole to the canister 226, while pacing therapy may use coils 196A and 198B as opposing electrodes for post-shock pacing therapy, with a still difference combination of electrodes used to provide ventricular pacing therapy for example by pacing between coil 196B and tip electrode 198C.

Line 202 is provided, illustratively, to separate the atria and ventricles. The lead 192 may be placed as shown such that the proximal coil 196A is about level with the ventricles, and distal coil 196B is about level with the atria, if desired. In some examples fewer or different electrodes may be provided on the lead 192 such as by excluding one or the other of the proximal coil 196A or distal coil 196B. Various designs are also shown herein.

Line 204 is provided to indicate the top of the heart, with the apex or bottom of the heart marked at 200. In some examples, one or more electrodes on the lead 192 are provided at or inferior to the apex 200, or at or superior to the top 204 of the heart. In the example shown, on the other hand, the electrodes are located generally between the apex 200 and top 204 of the heart.

The illustration shown in FIG. 4D places the lead on the left side 206 of the patient. In other examples, the right side 208 of the patient may instead or in addition be accessed, including the right ITV 210. Access to the right ITV 210 may be achieved by advancing the positioning mechanism 176 in a similar manner as described in regard to FIG. 4A. However, in this embodiment, the positioning mechanism 176 is advanced from the left subclavian access 170, across to the ostium of the right ITV 210. Alternatively, access to the right ITV may be achieved as shown by entering a right subclavian vein access point 230 in a mirror image procedure of that used to obtain the left subclavian access 170. In either example, once the distal end 184 of the positioning mechanism 176 is in the ITV 210, the positioning mechanism 176 may be located and an external access 228 may be established.

Once the distal end 184 of the positioning mechanism 176 is attached to the distal end 194 of the lead 192, advancement to the ITV 210 may be achieved by pulling the proximal end 186 of the positioning mechanism 176 from the access location 170, as shown by arrow 212, and drawing the lead 192 from the external access 228, into the right superior epigastric vein 310 (or alternatively the right musculophrenic vein), into the ITV 210, and advancing the lead 192 to a desired level within the ITV 210. Alternatively, advancement to the ITV 210 may be achieved by pulling the proximal end 186 of the positioning mechanism 176 from the access location 230, as shown by arrow 214, and drawing the lead 192 from the external access 228, into the right superior epigastric vein 310 (or the right musculophrenic vein), into the ITV 210, and advancing the lead 192 to a desired level within the ITV 210.

Figure 4E:
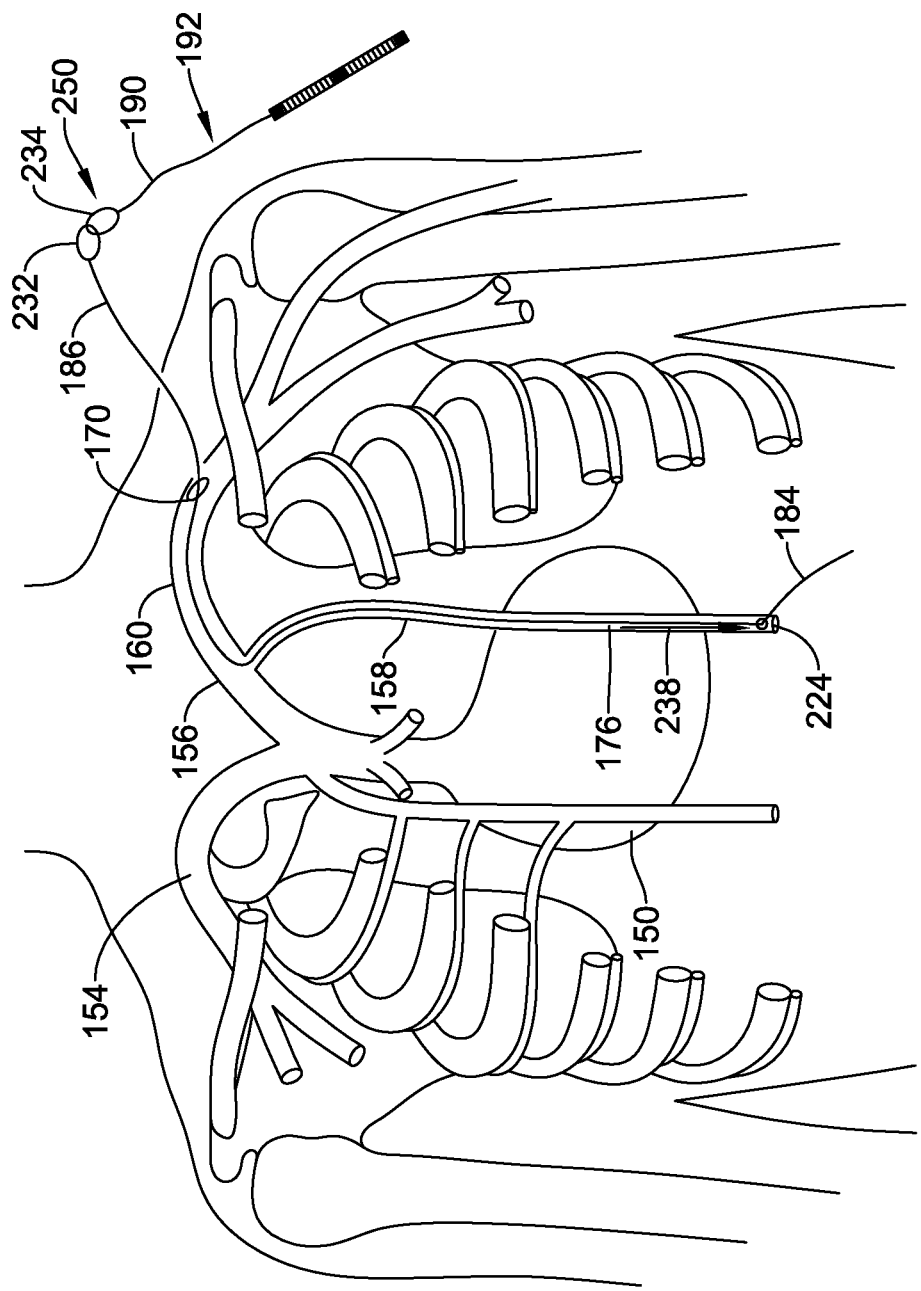

In another example, as shown in FIG. 4E, the distal end 184 of the positioning mechanism 176 may be similarly obtained through the external access 224. In this example, the proximal end 186 of the positioning mechanism 176 may include an attachment mechanism 232, similar to the attachment mechanism 188. In some cases, the proximal end 190 of the lead 192 may include a compatible attachment mechanism 234, similar to the compatible attachment mechanism 220, and configured to attach or couple to the attachment mechanism 232.

Once the proximal end 186 of the positioning mechanism 176 is attached to the proximal end 190 of the lead 192, advancement to the ITV 158 may be achieved by pulling the distal end 184 of the positioning mechanism 176 from the external access 224 location, as shown by arrow 238, and drawing the lead 192 from the access point 170, into the subclavian vein 160, to the brachiocephalic vein 156, through the ostium of the ITV 158, and advancing the lead 192 to a desired level within the ITV 158. In certain embodiments, the proximal end 190 of the lead 192 may have a connector 250 (e.g., a plug) configured to attach to the implantable pulse generator 226. In some cases, the connector 250 may have an adjustable shape that may assist in the advancement of the lead 192 through tight or tortuous anatomy. In some cases, the connector 250 may not have an adjustable shape, but is sized so that it is small enough to fit through tight or tortuous anatomy. When the lead 192 is at the desired level in the ITV 158, the lead 192 may be detached from the positioning mechanism 176.

Figure 4F:
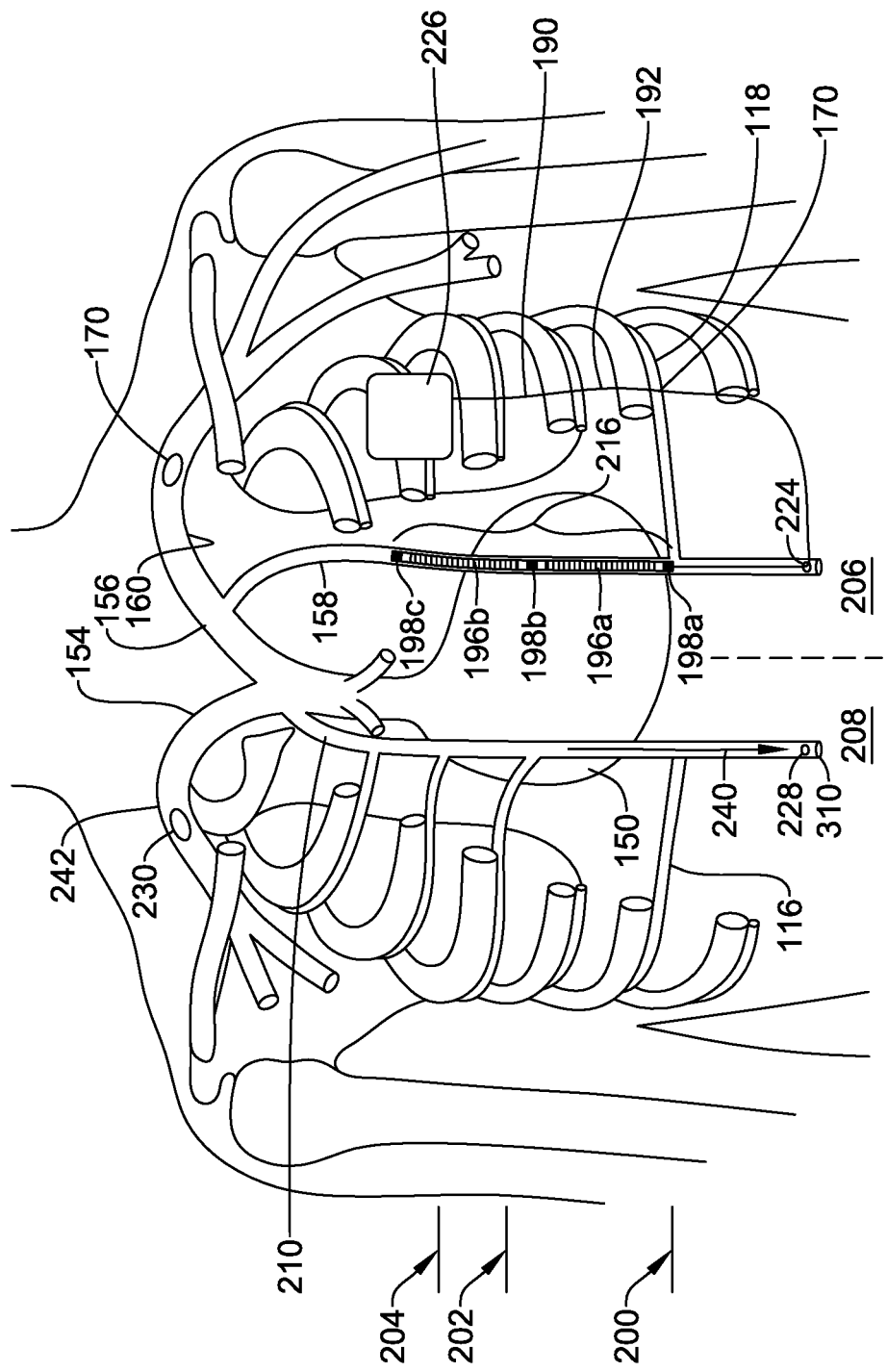

FIG. 4F shows another implantation of the implantable cardiac stimulus system. FIG. 4F is a replica of FIG. 4D and depicts how the implantation example described in regard to FIG. 4E can achieve similar results as the implantation example described in regard to FIGS. 4A-4C. Furthermore, the illustration shown in FIG. 4F places the lead on the left side 206 of the patient. In other examples, the right side 208 of the patient may instead or in addition be accessed, including the right ITV 210. Access to the right ITV 210 may be achieved by advancing the positioning mechanism 176 in a similar manner as described in regard to FIG. 4E. However, in this embodiment, the positioning mechanism 176 is advanced from the left subclavian access 170, across to the ostium of the right ITV 210. Alternatively, access to the right ITV may be achieved by entering the right subclavian vein access point 230 in a mirror image procedure of that used to obtain the left subclavian access 170. In either example, once the distal end 184 of the positioning mechanism 176 is in the ITV 210, the positioning mechanism 176 may be located and an external access 228 may be established.

Once the proximal end 186 of the positioning mechanism 176 is attached to the proximal end 190 of the lead 192, advancement to the ITV 210 may be achieved by pulling the distal end 184 of the positioning mechanism 176 from the external access 228 location, as shown by arrow 240, and drawing the lead 192 from the access point 170, into the subclavian vein 160, to the brachiocephalic vein 156, through the ostium of the right ITV 210, and advancing the lead 192 to a desired level within the right ITV 210. Alternatively, advancement to the right ITV 210 may be achieved by pulling the distal end 184 of the positioning mechanism 176 from the external access 228, as shown by arrow 240, and drawing the lead 192 from the access point 230, into a subclavian vein 242, to the brachiocephalic vein 154, through the ostium of the right ITV 210, and advancing the lead 192 to a desired level within the right ITV 210.

FIGS. 6A-6F show another example of access to and implantation of a lead in the ITV 158 by way of a tributary vein; in the example shown, a $6^{th}$ intercostal vein 600 is used. A different intercostal vein may be used if desired.

Many aspects of the implantation process are similar to the implantation process described with regard to FIGS. 4A-4F. Starting with FIG. 6A, access to the subclavian vein 160 is shown at 170 using standard access techniques known in the art for implanting traditional transvenous pacemakers and defibrillators, similar to the techniques described in regard to FIG. 4A. Into the access at 170, an introducer sheath 172 is inserted and advanced to a location to place its distal tip 180 near the ostium of the left ITV 158. Contrast injection may be useful to visualize the ITV structures and the ostia of the ITVs. The guide catheter 174 and the distal end 184 of the positioning mechanism 176 may then be introduced through the introducer sheath 172. In other examples, a shorter introducer sheath may be used, with the guide catheter 174 used to traverse the distance to the relevant ostium.

In certain embodiments, the positioning mechanism 176 may be a guidewire and may be the same as used in gaining initial access 170 (if one is used to gain access 170), or may be a different positioning mechanism. In an example, the positioning mechanism 176 is preloaded in the guide catheter and both are introduced at the same time until the guide catheter 174 is at a desired location relative to the ostium of the selected ITV. The distal end 184 of the positioning mechanism 176, which may be deflectable or steerable, can then be used to enter the left ITV 158 through the ostium thereof, passing down into the left ITV 158, then enter an ostium from the left ITV 158 into the selected intercostal vein 600.

In some examples, the guide catheter 174 is introduced first and the positioning mechanism 176 is introduced next. For example, a steerable or curved guide catheter 174 may traverse the introducer sheath 172 to its distal end 180 and then, using steering of the guide catheter or a precurved structure of the guide catheter, would then turn as shown at 182 to enter the left ITV 158. The positioning mechanism 176 may then be introduced through the guide catheter 174, advanced into the left ITV 158, passing down into the left ITV 158, then enter the ostium from the left ITV 158 into the intercostal vein 600.

Figure 6A:
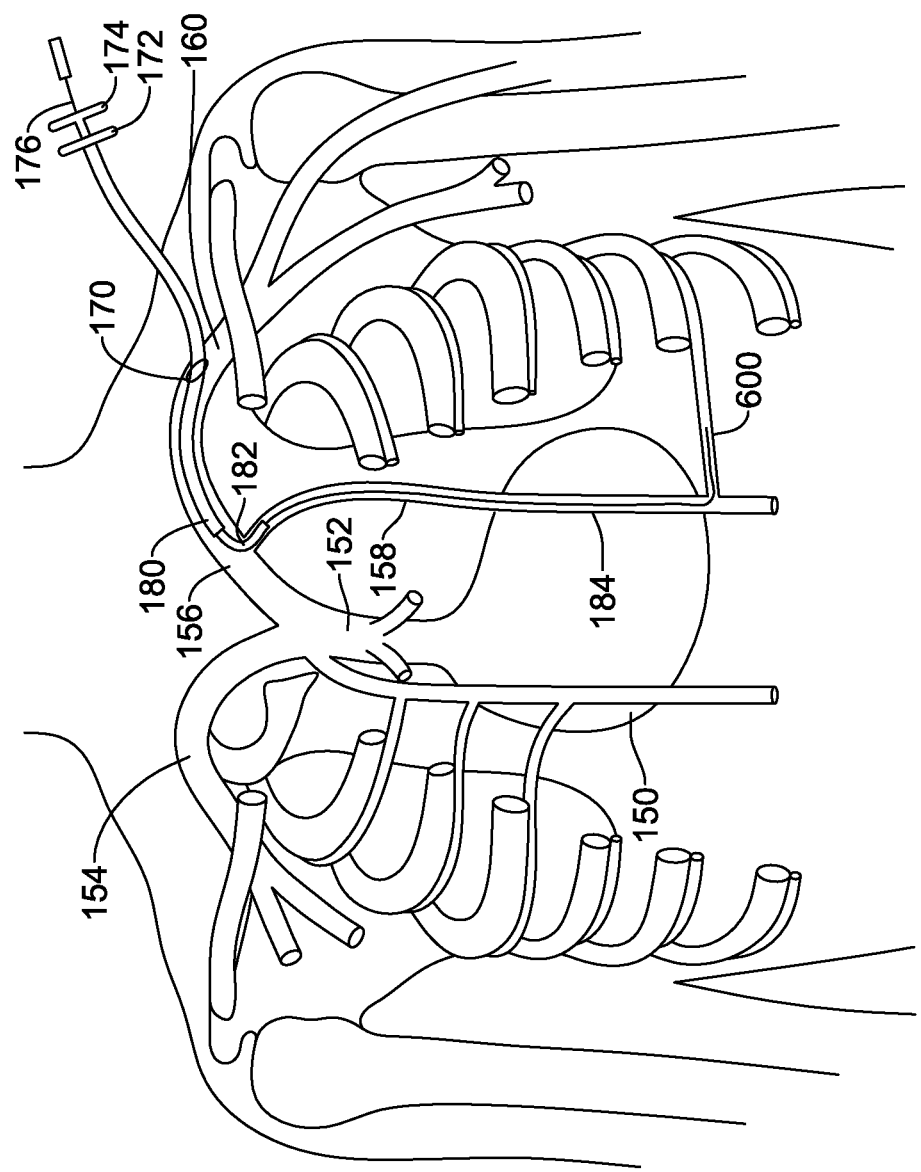
FIGS. 6A-6F show access to and implantation of a lead in the left ITV by way of an intercostal vein.
Figure 6B:
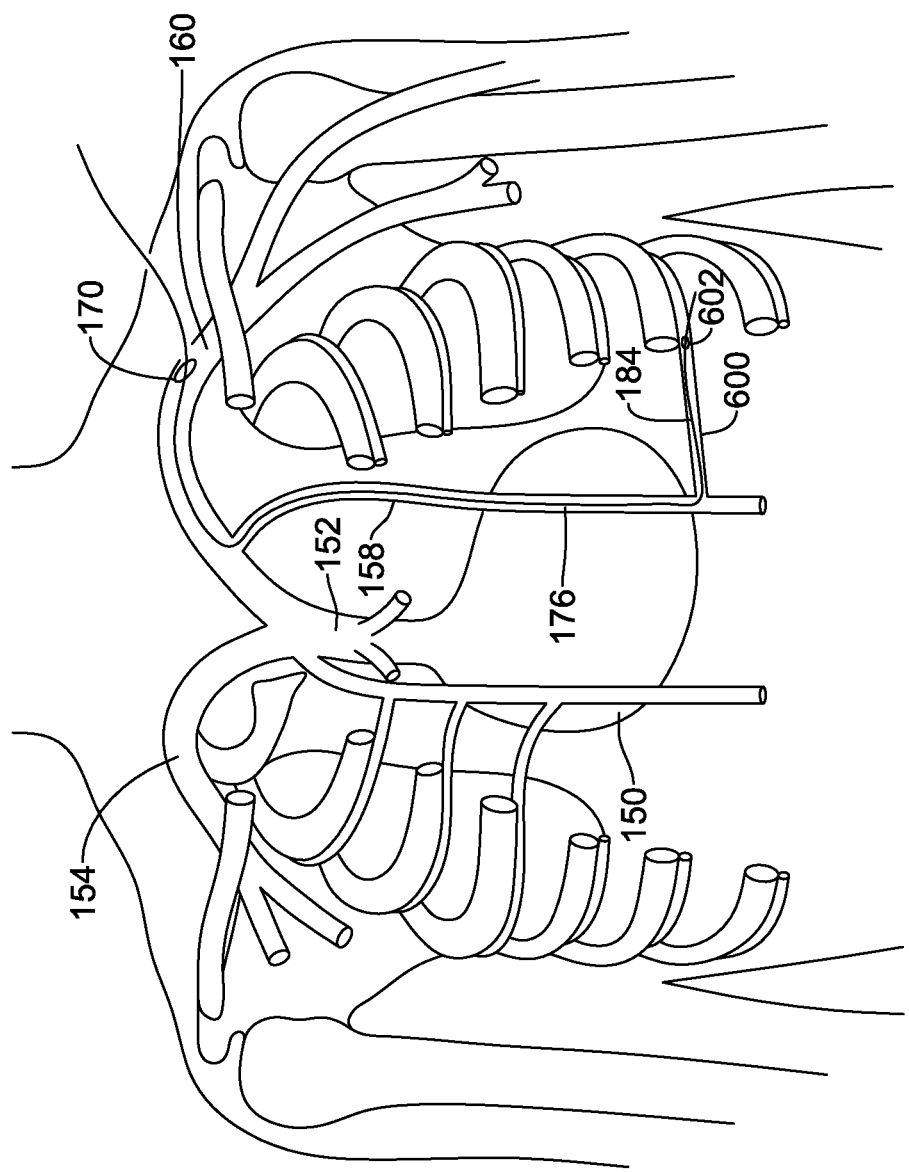

FIG. 6B shows the distal end 184 of the positioning mechanism 176 in the intercostal vein 600. In some cases, the presence of the positioning mechanism 176 inside the intercostal vein 600 may disclose the location of the intercostal vein 600 and increase the accuracy of establishing an external access 602 in the intercostal vein 600. As a result, the positioning mechanism 176 may be located (e.g., using visualization techniques described herein) inside the intercostal vein 600.

Figure 6C:
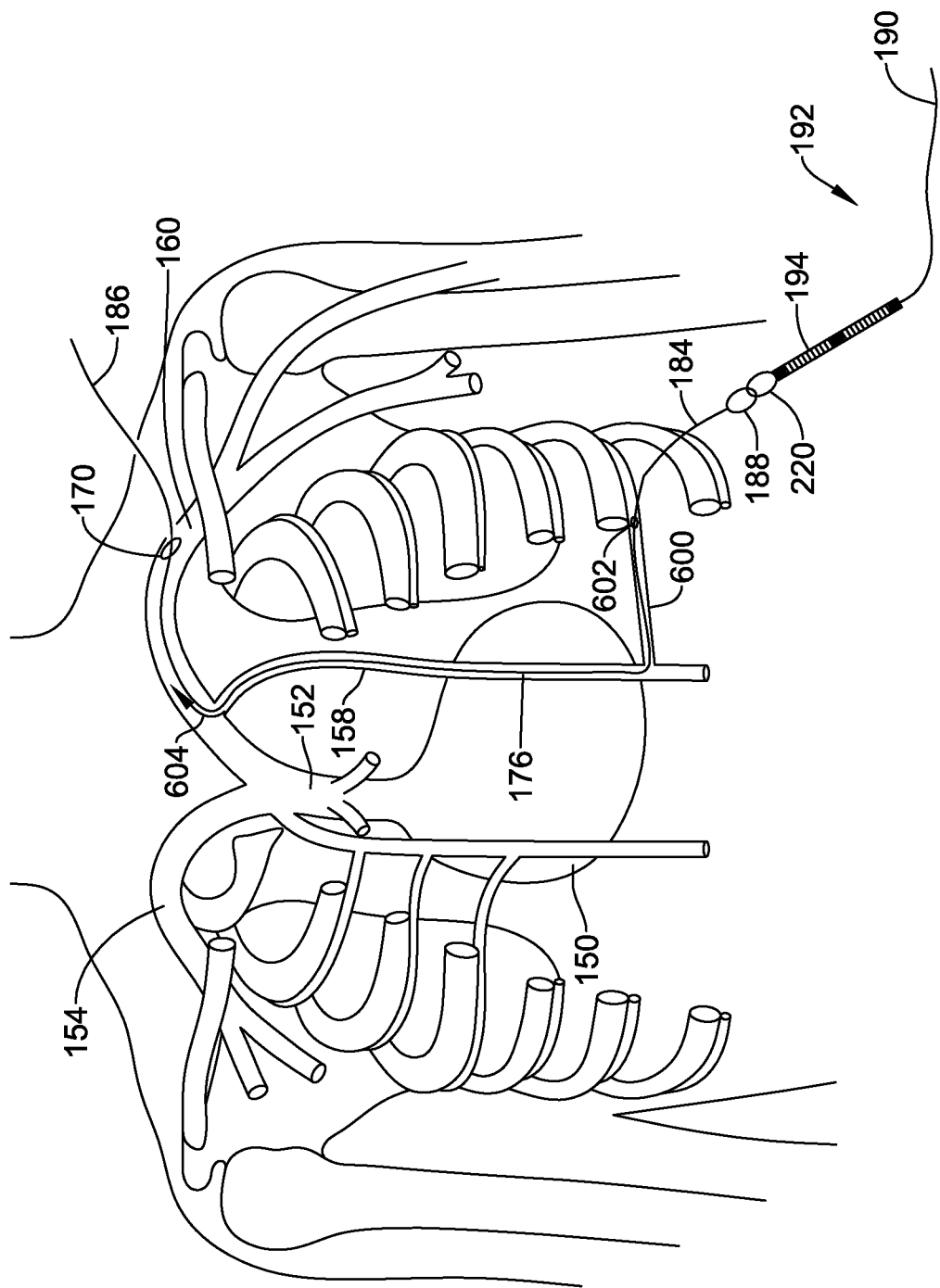

In certain embodiments, as shown in FIG. 6C, the distal end 184 of the positioning mechanism 176 may be obtained through the external access 602. In some cases, the distal end 184 of the positioning mechanism 176 may include the attachment mechanism 188 with shape adjustment capabilities. In some cases, the distal end 194 of the lead 192 may include the compatible attachment mechanism 220 that may be configured to attach or couple to the attachment mechanism 188. Once the distal end 184 of the positioning mechanism 176 is attached to the distal end 194 of the lead 192, advancement to the ITV 158 may be achieved by pulling the proximal end 186 of the positioning mechanism 176 from the access location 170, as shown by arrow 604, and drawing the lead 192 from the external access 602, into the intercostal vein 600, to the ITV 158, and advancing the lead 192 to a desired level within the ITV 158. As previously stated, in various embodiments, the lead 192 may be protected by a cover or cap before implantation.

Figure 6D:
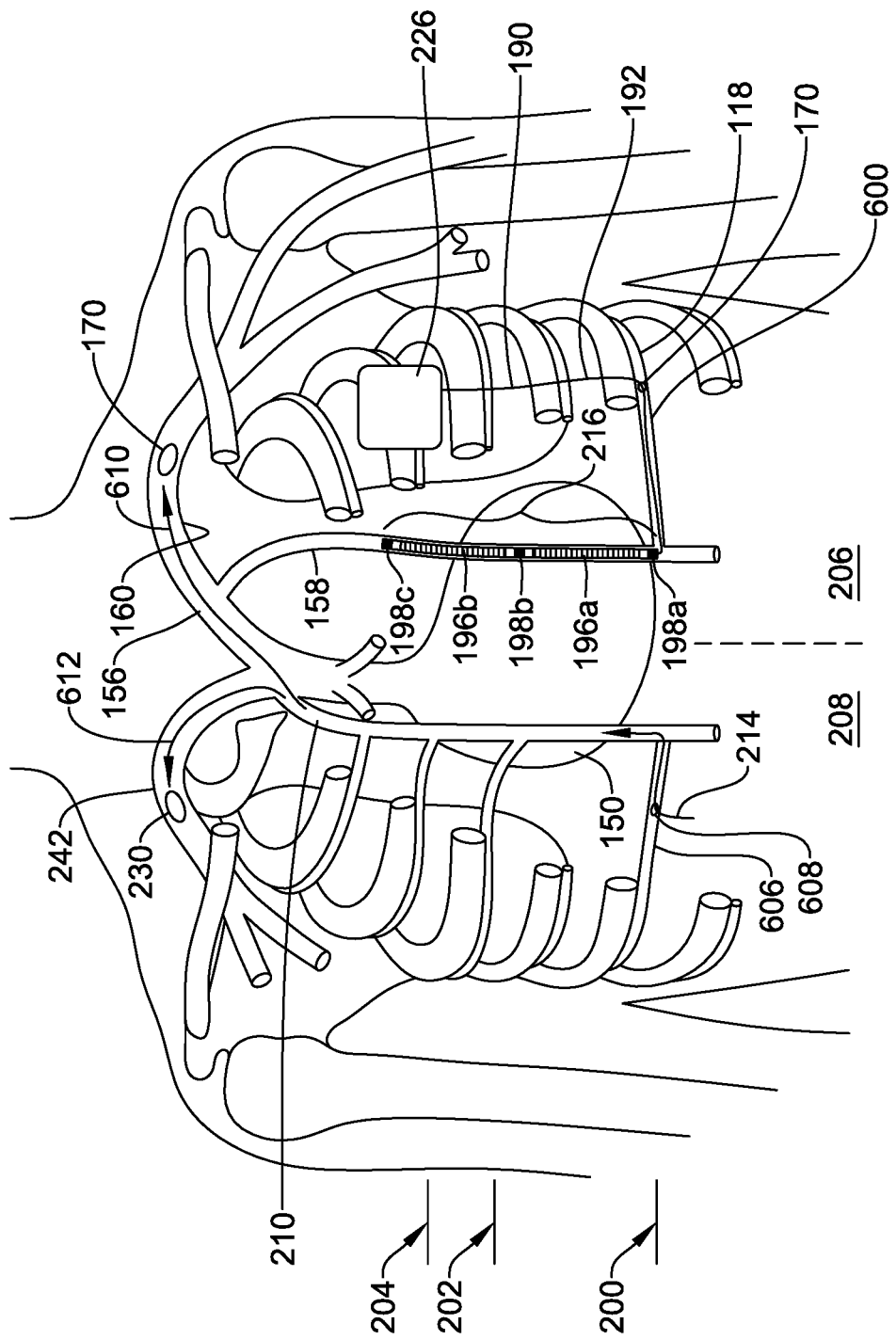

FIG. 6D shows another implantation of the implantable cardiac stimulus system. FIG. 6D is similar to FIGS. 4D and 4F and depicts how the implantation example described in regard to FIGS. 6A-6C can achieve similar results as the implantation exampled described in regard to FIGS. 4A-4C and 4D. However, in this case, the lead 192 may have a proximal end 190 configured to extend from the intercostal vein 600 and attach to the implantable pulse generator 226. Moreover, in some cases, the implantable pulse generator 226 may be implanted near the clavicle of the patient. In some cases the implantable pulse generator 226 may be placed at the high-pectoral or traditional transvenous position. In some cases, the implantable pulse generator 226 may be placed at approximately the left axilla. For example, the implantable pulse generator 226 may be placed at the anterior axillary line, the midaxillary line, or in the posterior axillary line.

In certain embodiments, the distal end 194 of the lead 192 may be configured to have a first portion deployed within the ITV 158 and a second portion deployed within the intercostal vein 600. In other cases, a first lead having an electrode structure may be configured to be deployed within the ITV 158 and a second lead having an electrode structure may be configured to be deployed within the intercostal vein 600. For example, a shock coil may reside in the intercostal vein 600.

The illustration shown in FIG. 6D places the lead on the left side 206 of the patient. In other examples, the right side 208 of the patient may instead or in addition be accessed, including the right ITV 210. Access to the right ITV 210 may be achieved by advancing the positioning mechanism 176 in a similar manner as described in regard to FIG. 6A. However, in this embodiment, the positioning mechanism 176 is advanced from the left subclavian access 170, across to the ostium of the right ITV 210, through the right ITV 210, and into the ostium of an intercostal vein 606. Alternatively, access to the right ITV 210 may be achieved as shown by entering the right subclavian vein access point 230 in a mirror image procedure of that used to obtain the left subclavian access 170. In either cases, once the distal end 184 of the positioning mechanism 176 is in the intercostal vein 606, the positioning mechanism 176 may be located and an external access 608 may be established.

Once the distal end 184 of the positioning mechanism 176 is attached to the distal end 194 of the lead 192, advancement to the ITV 210 may be achieved by pulling the proximal end 186 of the positioning mechanism 176 from the access location 170, as shown by arrow 610, and drawing the lead 192 from the external access 608, into the intercostal vein 606, into the ITV 210, and advancing the lead 192 to a desired level within the ITV 210. Alternatively, advancement to the ITV 210 may be achieved by pulling the proximal end 186 of the positioning mechanism 176 from the access location 230, as shown by arrow 612, and drawing the lead 192 from the external access 228, into the intercostal vein 606, into the ITV 210, and advancing the lead 192 to a desired level within the ITV 210.

In some examples, rather than accessing the ITV from an intercostal vein at a relatively lower part of the chest as shown in FIG. 6D, the ITV may be accessed in a more superior position, such as near the $2^{nd}$ to $4^{th}$ ribs, or about level with the location of the implantable pulse generator 226. From this more superior entry to the ITV, the lead 192 may then be passed inferiorly to place shock, sensing and/or pacing electrodes at a desired level relative to the patient's heart. In still other examples, an intermediate position may be selected and a lead or leads passed inferiorly and superiorly. In still further examples, first and second intercostal veins may be accessed to provide two entry points into the ITV, allowing a first lead implanted via a first intercostal vein to be advanced in a superior direction, and a second lead implanted via a second intercostal vein to be advanced in an inferior direction.

Figure 6E:
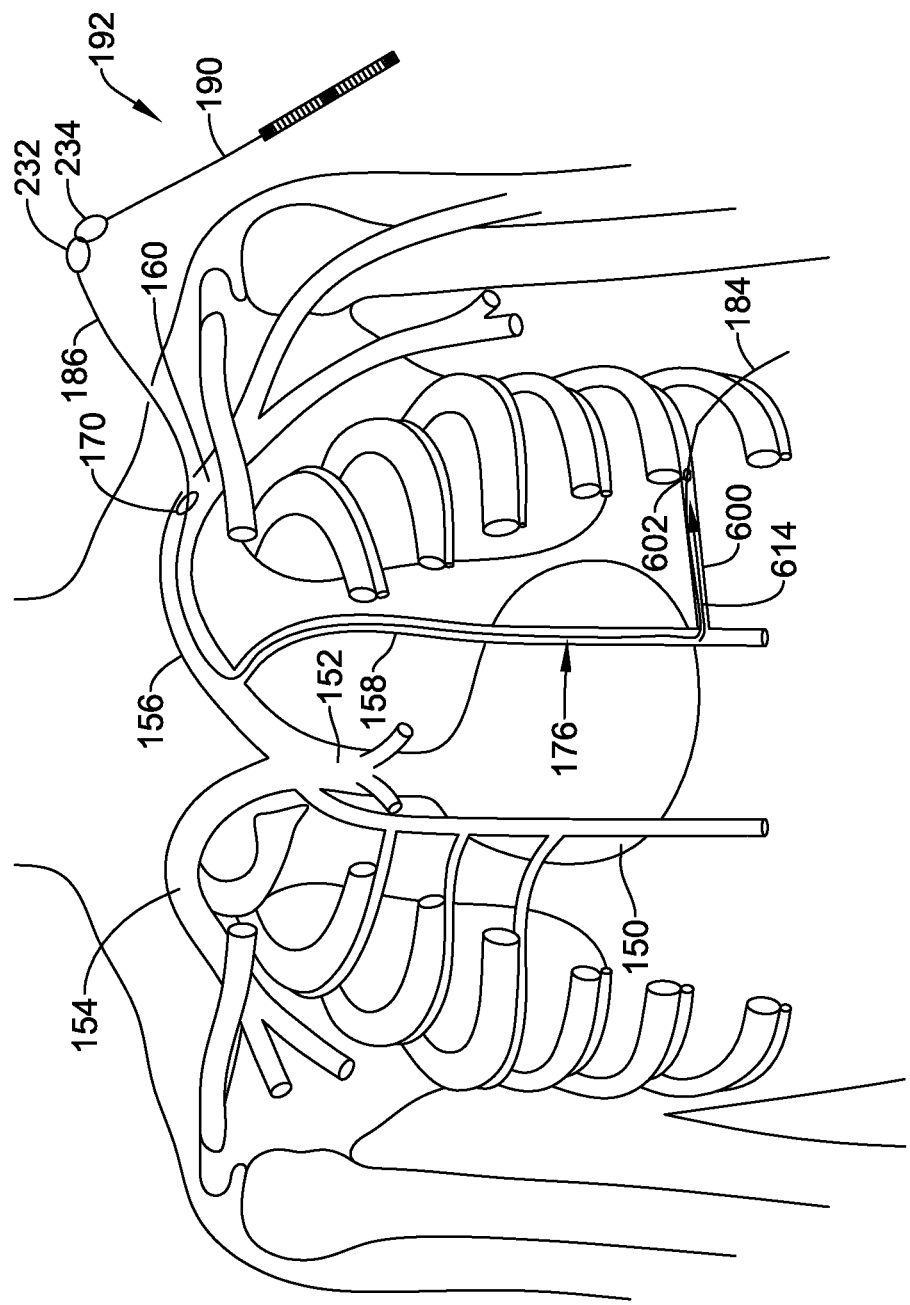

In another example, as shown in FIG. 6E, the distal end 184 of the positioning mechanism 176 may be similarly obtained through the external access 602. In some cases, the proximal end 186 of the positioning mechanism 176 may include the attachment mechanism 232, the proximal end 190 of the lead 192 may include the compatible attachment mechanism 234, and the compatible attachment mechanism 234 may be configured to attach or couple to the attachment mechanism 232.

Once the proximal end 186 of the positioning mechanism 176 is attached to the proximal end 190 of the lead 192, advancement to the ITV 158 may be achieved by pulling the distal end 184 of the positioning mechanism 176 from the external access 602 location, as shown by arrow 614, and drawing the lead 192 from the access point 170, into the subclavian vein 160, to the brachiocephalic vein 156, through the ostium of the ITV 158, and advancing the lead 192 to a desired level within the ITV 158. In certain embodiments, at least a portion of the lead 192 may be further advanced through the ITV 158, into the ostium of the intercostal vein 600, and then advanced to a desired location within intercostal vein 600.

Figure 6F:
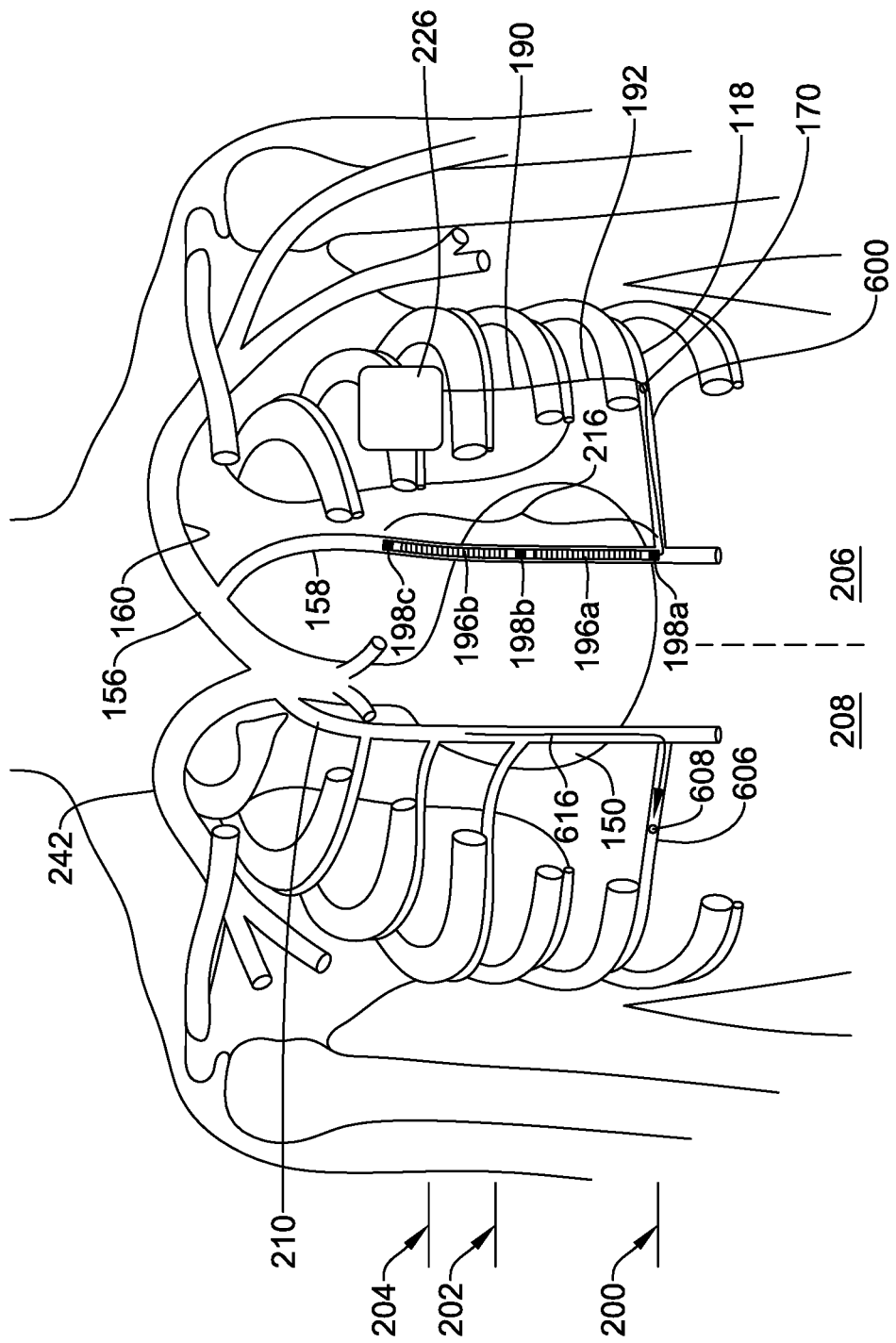

FIG. 6F shows another implantation of the implantable cardiac stimulus system. FIG. 6F is a replica of FIG. 6D and depicts how the implantation example described in regard to FIG. 6E can achieve similar results as the implantation example described in regard to FIGS. 6A-6C. Accordingly, variations in the electrode structures included on the lead 192 and variations in the implantation locations and configurations of the lead 192, as described in regard to FIG. 6D, also apply to FIG. 6F.

Furthermore, the illustration shown in FIG. 6F places the lead on the left side 206 of the patient. In other examples, the right side 208 of the patient may instead or in addition be accessed, including the right ITV 210. Access to the right ITV 210 may be achieved by advancing the positioning mechanism 176 in a similar manner as described in regard to FIG. 6A. However, in this embodiment, the positioning mechanism 176 is advanced from the left subclavian access 170, across to the ostium of the right ITV 210, through the right ITV 210, into the ostium of an intercostal vein 606. Alternatively, access to the right ITV 210 may be achieved as shown by entering the right subclavian vein access point 230 in a mirror image procedure of that used to obtain the left subclavian access 170. In either cases, once the distal end 184 of the positioning mechanism 176 is in the intercostal vein 606, the positioning mechanism 176 may be located and the external access 608 may be established.

Once the proximal end 186 of the positioning mechanism 176 is attached to the proximal end 190 of the lead 192, advancement to the ITV 210 may be achieved by pulling the distal end 184 of the positioning mechanism 176 from the external access 608 location, as shown by arrow 616, and drawing the lead 192 from the access point 170, into the subclavian vein 160, to the brachiocephalic vein 156, through the ostium of the ITV 210, and advancing the lead 192 to a desired level within the ITV 210. In certain embodiments, at least a portion of the lead 192 may be further advanced through the ITV 210, into the ostium of the intercostal vein 606, and advanced to a desired location within the intercostal vein 606. Alternatively, advancement to the ITV 210 may be achieved by pulling the distal end 184 of the positioning mechanism 176 from the external access 608 location, as shown by arrow 616, and drawing the lead 192 from the access point 230, into the subclavian vein 242, to the brachiocephalic vein 154, through the ostium of the right ITV 210, and advancing the lead 192 to a desired level within the right ITV 210. Similarly, in certain embodiments, at least a portion of the lead 192 may be further advanced through the ITV 210, into the ostium of the intercostal vein 606, and advanced to a desired location within intercostal vein 606.

Figure 7:
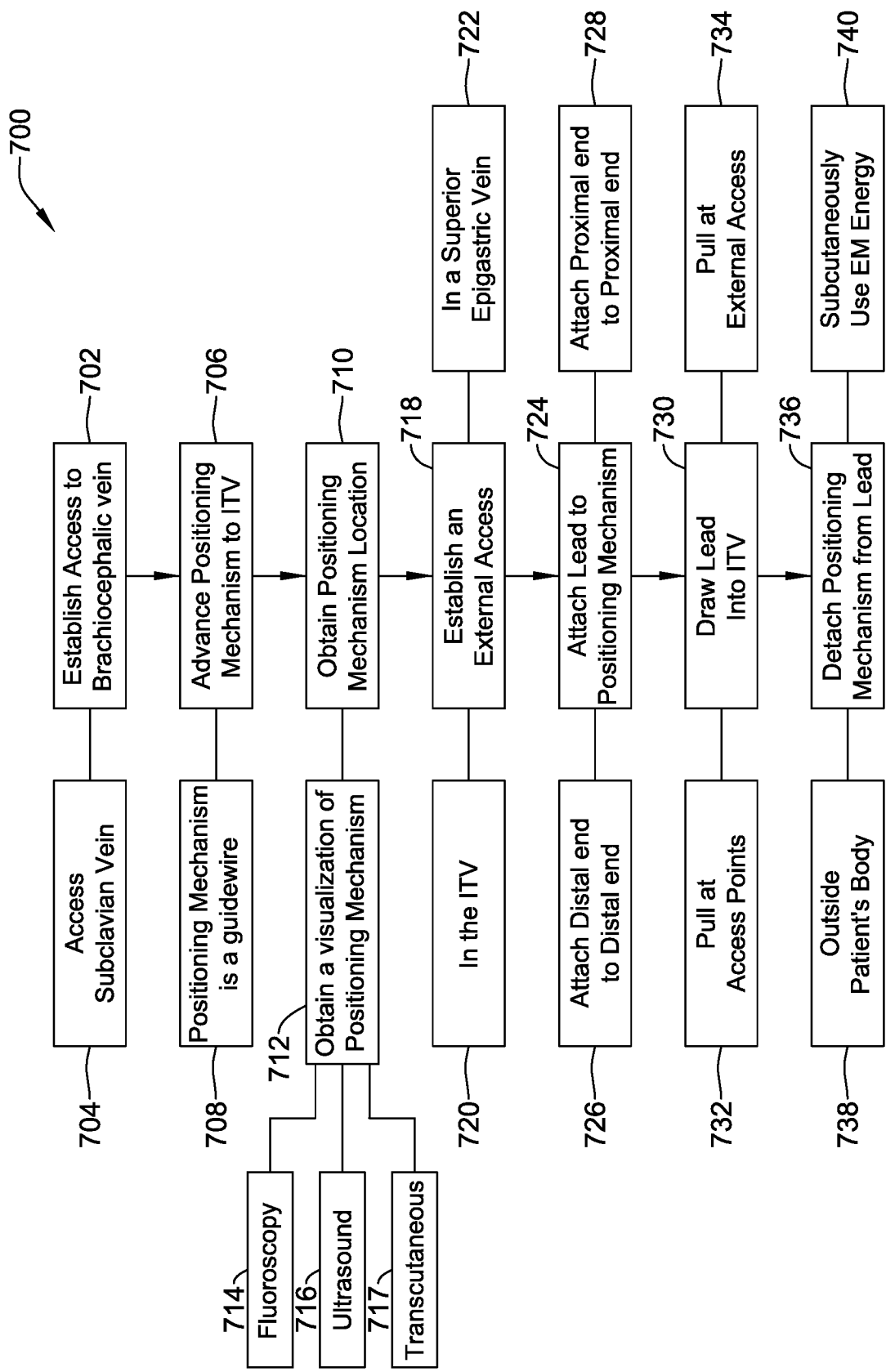
FIG. 7 is a block flow diagram for an illustrative method.

FIG. 7 is a block flow diagram for an illustrative method for implanting a lead in an ITV. As shown at 700, the method comprises establishing access to a brachiocephalic vein 702, advancing a positioning mechanism to an ITV 706, obtaining the positioning mechanism location 710, establishing an external access 718, attaching a lead to the positioning mechanism 724, drawing the lead into the ITV 730, and detaching the positioning mechanism from the lead 736.

For example, establishing access to the brachiocephalic vein 702 may include accessing a subclavian vein 704 and advancing into the brachiocephalic vein. Access to the subclavian vein may be done using standard access techniques known in the art for implanting traditional transvenous pacemakers and defibrillators. For example, the Seldinger technique may be used or other venipuncture or cutdown techniques. Other vessels may be accessed instead of the subclavian vein using similar techniques including, for example, the jugular, cephalic, or axillary veins.

In an example, advancing the positioning mechanism to the ITV 706 may include passing through an ostium of the ITV in the brachiocephalic vein. In some examples, the positioning mechanism may be a guidewire 708 and may be the same as used in establishing access to the brachiocephalic vein 702 The positioning mechanism may be instead a stylet, a hypotube, or a catheter having sufficient column strength to allow pushing through blood vessels to desired position, and further with sufficient strength to allow pulling of a lead. In another example, the positioning mechanism may be a combination of a guide catheter and guidewire and are introduced at the access location and the guide catheter is advanced to a desired location relative to the ostium of the ITV. The positioning mechanism, which may be deflectable or steerable, can then be used to enter the ITV through the ostium thereof, passing down into the ITV. Furthermore, in some examples, a distal end of the positioning mechanism may have an adjustable shape that may assist the positioning mechanism in advancing through tight or tortuous anatomy.

In an example, obtaining the positioning mechanism location 710 may include obtaining a visualization of the positioning mechanism 712. In some examples, the positioning mechanism may be a radiopaque guidewire. In other cases, a radiopaque material may be placed over the positioning mechanism. When the positioning mechanism is inside the ITV the positioning mechanism may then be visualized, for example, using fluoroscopy 714, an ultrasound 716, or an LED may be positioned at or near the distal tip of the positioning mechanism to allow transcutaneous visualization 717. The positioning mechanism may then be observed and adjusted inside the ITV to a desired location. In some examples, a physician may use the fluoroscope image to identify the positioning mechanism and place forceps in the view range of the fluoroscope to get a surface position of the positioning mechanism. In some examples, the surface position of the positioning mechanism may be obtained using fluoroscope imaging to identify the positioning mechanism and an x-ray may be used to identify the xiphoid. In some cases, instead of an x-ray, ultrasound imaging may be used to identify the xiphoid. In some cases, fluoroscopy may not be used and ultrasound imaging may be used to identify the positioning mechanism and the physician may use an ultrasound needle in the view range of the ultrasound to establish the position of the positioning mechanism. In still further embodiments, a special positioning mechanism may be used that discloses its position in some shape or form in the ITV.

In an example, establishing an external access 718 may include using one of the visualization techniques described above or another conventional locating or visualization technique known by those skilled in the art to establish the external access position in the ITV 720 or in a musculophrenic or superior epigastric vein 722.

In an example, attaching the lead to the positioning mechanism 724 may include attaching a distal end of the lead to the distal end of the positioning mechanism 726. In some examples, the distal end of the positioning mechanism may be obtained through the external access and the distal end of the positioning mechanism may have an attachment mechanism and the distal end of the lead may have a compatible attachment mechanism, such as a suture hole. In some examples, the distal end of the lead may be attached to the distal end of the positioning mechanism by using a suture to removably secure the suture hole of the lead to the positioning mechanism. In another example, a proximal end of the lead may be attached to a proximal end of the positioning mechanism 728. In some examples, the distal end of the positioning mechanism may be obtained through the external access and the proximal end of the positioning mechanism may have an attachment mechanism and the proximal end of the lead may have a compatible attachment mechanism, such as a suture hole. In some examples, the proximal end of the lead may be attached to the proximal end of the positioning mechanism by using a suture to removeably secure the suture hole of the lead to the positioning mechanism.

In an example, drawing the lead into the ITV 730 may include pulling the proximal end of the positioning mechanism 732. In some examples, the proximal end of the positioning mechanism may be located near the access point of the brachiocephalic vein and advancement of the lead may be achieved by pulling the proximal end of the positioning mechanism from the access point and drawing the lead from the external access, into the left superior epigastric vein (or the left musculophrenic vein), to the ITV, and pulling or advancing the superiorly lead to a desired level within the ITV. In another example, drawing the lead into the ITV 730 may include pulling the distal end of the positioning mechanism 734. In some examples, the distal end of the positioning mechanism may be located near the external access position and advancement to the ITV may be achieved by pulling the distal end of the positioning mechanism from the external access location, and drawing the lead inferiorly from the superior access point, into the subclavian vein, to the brachiocephalic vein, through the ostium of the ITV, and advancing the lead to a desired level within the ITV.

In an example, detaching the positioning mechanism from the lead 736 may include detaching the positioning mechanism from the lead outside of the patient's body 738. In some cases, an incision may be made to detach the lead from the positioning mechanism. In some cases, the lead may be detached from the positioning mechanism subcutaneously 740. In some examples, electromagnetic energy (e.g., RF energy) may be used to break the bond between the lead and the positioning mechanism.

Figure 8:
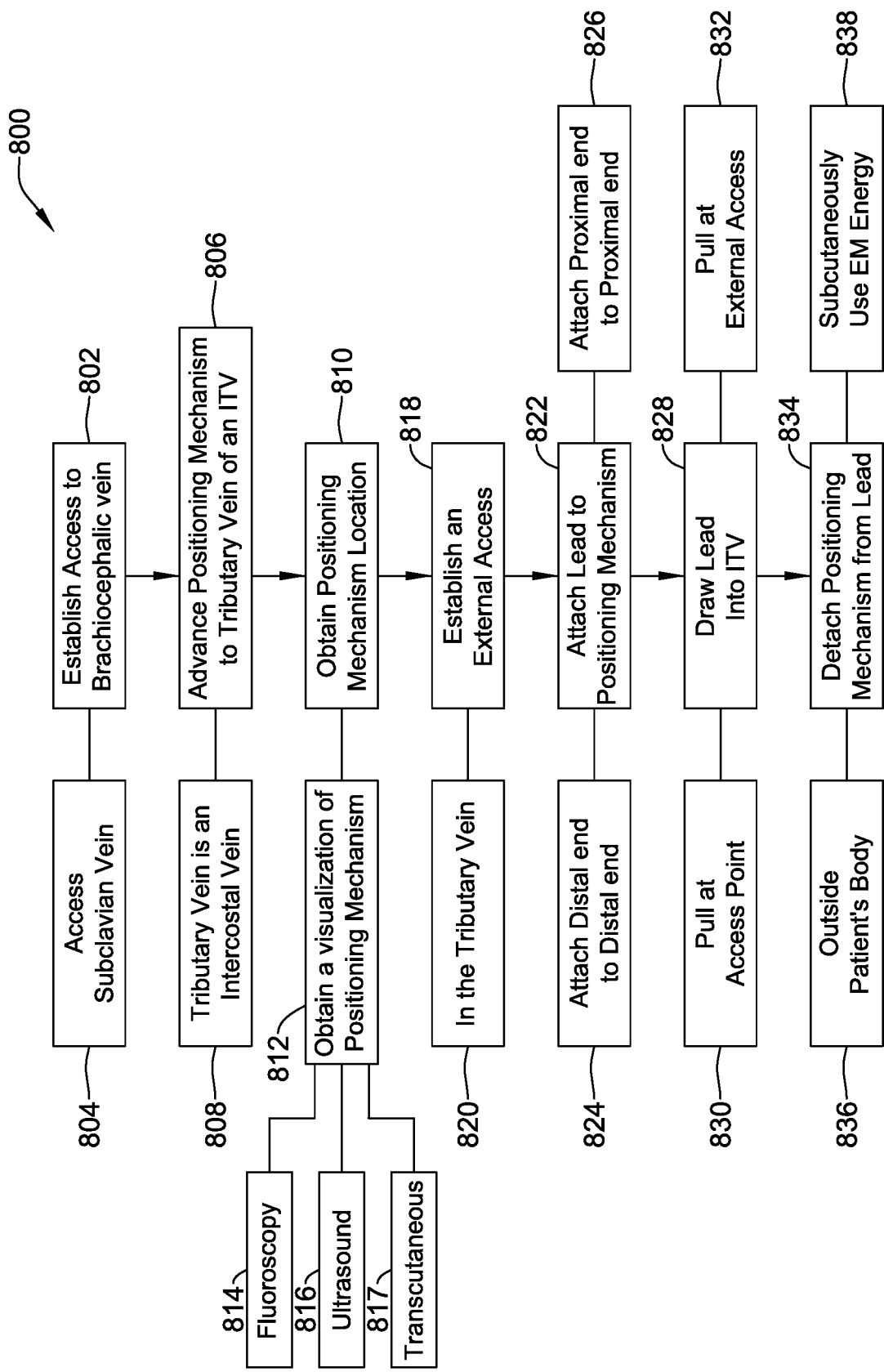
FIG. 8 is a block flow diagram for another illustrative method.

FIG. 8 is a block flow diagram for an illustrative method for implanting a lead in an ITV by way of a tributary vein. As shown at 800, the method comprises establishing access to a brachiocephalic vein 802, advancing a positioning mechanism 806, obtaining the positioning mechanism location 810, establishing an external access 818, attaching a lead to the positioning mechanism 822, drawing the lead into the ITV ix) 828, and detaching the positioning mechanism from the lead 834.

For example, establishing access to the brachiocephalic vein 802 may be done similar to the examples discussed in regard to step 702, of flow diagram 700. In an example, advancing the positioning mechanism to a tributary vein of the ITV 806 may be done similar to the examples discussed in regard to step 706, of flow diagram 700. Furthermore, the tributary vein may be an intercostal vein 808 and the advancement of the positioning mechanism may further include passing down into the ITV, and entering an ostium from the ITV into the intercostal vein. In an example, obtaining the positioning mechanism location 810 may be done similar to the examples discussed in regard to step 710, of flow diagram 700. In an example, establishing an external 818 may be done similar to the examples discussed in regard to step 718, of flow diagram 700. However, in this case, the visualization techniques or other conventional locating or visualization techniques known by those skilled in the art may be used to establish the external access position in the tributary vein 820 (e.g., the intercostal vein). In an example, attaching the lead to the positioning mechanism 822 may be done similar to the examples discussed in regard to step 724, of flow diagram 700.

In an example, drawing the lead into the ITV 828 may include pulling the proximal end of the positioning mechanism 830. In some examples, the proximal end of the positioning mechanism may be located near the access point of the brachiocephalic vein and advancement to the ITV may be achieved by pulling the proximal end of the positioning mechanism from the access point, and drawing the lead from the external access, into the intercostal vein, to the ITV, and advancing the lead to a desired level within the ITV. In another example, drawing the lead into the ITV 828 may include pulling the distal end of the positioning mechanism 832. In some examples, the distal end of the positioning mechanism may be located near the external access position and advancement to the ITV may be achieved by pulling the distal end of the positioning mechanism from the external access location, and drawing the lead from the access point, into the subclavian vein, to the brachiocephalic vein, through the ostium of the ITV, and advancing the lead to a desired level within the ITV.

In an example, detaching the positioning mechanism from the lead 834 may be done similar to the examples discussed in regard to step 736, of flow diagram 700.

Some embodiments of the present invention may take the form of an implantation tool set configured for use in implanting a cardiac device, such as a lead, into an ITV. Some such embodiments may include an introducer sheath. Some such embodiments may include a guide catheter. Some such embodiments may include a guidewire. Some such embodiments may further include a tool set for performing a Seldinger technique to access a blood vessel percutaneously.

Some embodiments of the present invention take the form of an implantable cardiac stimulus device comprising a lead and an implantable canister for coupling to the lead, the implantable canister housing operational circuitry configured to deliver output therapy in the form of at least one of bradycardia pacing, anti-tachycardia pacing, cardiac resynchronization therapy, or defibrillation, using a lead implanted in an ITV and a canister implanted in a patient.

Figure 9:
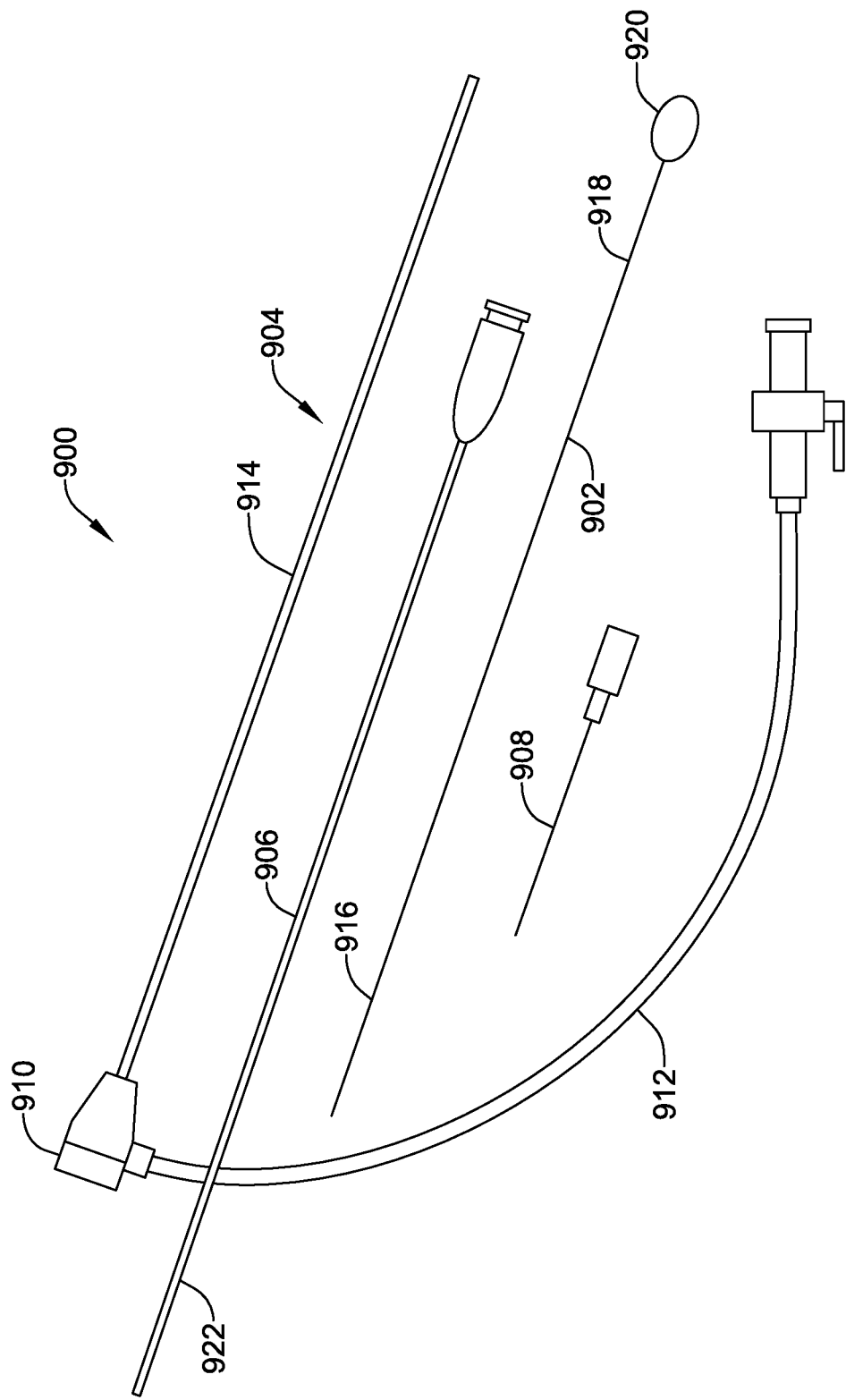
FIG. 9 shows an illustrative lead insertion tool set.

FIG. 9 illustrates an exemplary implantation tool set 900 for use in implantation of a lead in the ITV, as described herein. As shown, in various embodiments, the implantation tool set 900 may include a positioning mechanism 902, an introducer sheath 904, a dilator 906, and a hollow needle 908. In some examples, the needle 908 may be used to make an incision by inserting the needle 908 through a patient's skin and any intervening tissue into the vascular system. The dilator 906, having a tapered end 922, may then be advanced through the tissue to enlarge the opening at the access location. Once the tissue is enlarged, the positioning mechanism 902 may be passed through the needle 908 lumen into the patient's blood vessel.

The positioning mechanism 902 may be fabricated by methods well known in the art. In certain embodiments, the positioning mechanism 902 may be a guidewire, a stylet, a hypotube, or a catheter. In some cases, the positioning mechanism 902 may be formed from any high tensile strength material such as stainless steel, titanium, or a suitable superelastic nickel-titanium (NiTi) alloy, and may be formed through methods such as multiple extrusion of a tube through repeatedly smaller dies until the desired dimensions are achieved. In various embodiments, the positioning mechanism may have the characteristics of "pushability", "pullability", and "torqueability" that allow it to be pushed along tortuous paths defined by the body lumens in which it is intended to be used. In some cases, the positioning mechanism 902 may be constructed of a polymer or have composite distal portion secured to a metal alloy proximal portion by any suitable method such as welding, brazing, or use of epoxies. Such construction would combine the "pushability", "pullability", and "torqueability" characteristics of metal over substantially the length of the positioning mechanism 902, with the flexibility inherent to polymers at its distal extremity, thereby facilitating the insertion and positioning of the guide wire within the patient's vascular system. In some cases, the positioning mechanism 902 or a portion of the positioning mechanism 902 may be composed of a radiopaque material to assist in positioning of the positioning mechanism 902 within the blood vessels. In other cases, a radiopaque material may be placed over the positioning mechanism 902 or a portion thereof. In still further embodiments, an illuminating element such as an LED may be positioned at or near the tip of a proximal end 916 or a distal end 918 of the positioning mechanism 902 to allow ready transcutaneous visualization thereof.

According to various embodiments, the positioning mechanism 902 may have a suitable outer diameter, such as in the range of 0.008 to 0.032, for example, so that it may be utilized to negotiate the complex vascular system of a patient to guide a medical device, (e.g. a lead) to a desired location in the ITV. The positioning mechanism 902 shown in FIG. 9 has a constant outer diameter along its entire length, but it will be understood by those skilled in the art that positioning mechanism 902 also may be formed in a tapering configuration having a larger outer diameter at the proximal end 916 and a smaller diameter at the distal end 918 or vice versa. In some cases, the overall length of the positioning mechanism 902 may be in the range from 50 to 250 centimeters. However, this is only an example and other lengths are contemplated.

In certain embodiments, the distal end 918 may include a coupler 920 that may include, an eyelet or a suture with a suture hole or holes, a hook, a snare, a threaded screw, pins, or any other suitable means of attaching the positioning mechanism 902 to a medical device, (e.g. a lead). In other embodiments, the coupler 920 may be located at the proximal end 916 of the positioning mechanism. Moreover, in certain embodiments, the coupler 920 may be coupled to the positioning mechanism 902. In other embodiments, the positioning mechanism 902 and the coupler 920 may be a formed, single-piece. In some cases, the coupler 920 may have an adjustable shape. For example, the shape of the coupler 920 may change from a compressed state that may assist in advancing the positioning mechanism 902 through tight or tortuous anatomy to an expanded state that may assist the positioning mechanism 902 in attachment capabilities.

According to various embodiments, the sheath 904 may also be fabricated by methods well known in the art. In some cases, the sheath 904 may include only a single channel body 914 having an inner diameter from 4 mm to 10 mm and a thin wall between 0.25 mm to 1 mm, for example. In certain embodiments, the body 914 may extend between 30 cm and 60 cm, but may vary as needed and can depend on several factors, such as the initial access location created by the needle 908, for example. In some situations, the body 914 may have sufficient strength in order to avoid kinking and collapsing during use, even when the body 914 is bent through a small radius curve. The body 914 may also have sufficient column strength so that it can be advanced through restricted passages. To meet these mechanical requirements, in various embodiments, the body 914 may be reinforced, such as by an embedded metal coil, braid, filament(s), or the like. In some cases, the body 914 may be reinforced with a helical coil formed from a flat metal ribbon, such as a stainless steel ribbon. In some cases, the body 914 may have an inner tubular liner that is formed from a lubricous material, such as polytetrafluoroethylene (PTFE), fluorinated ethylenepropylene polymer (FEP), polyether block amide copolymer (pebax), polyamide (nylon), polyethylene, and the like. The inner liner may also be formed from a non-lubricous material, such as a polyurethane and the inner liner may be coated with a lubricating material, such as a silicone gel. In some examples, the lubricating layer may also be used with other, more lubricous materials, in order to provide even greater lubricity for the introduction of instruments and devices, such as the positioning mechanism 902, through the sheath 904. In certain embodiments, an outer plastic coating may be disposed over the inner tubular liner. The plastic coating may be composed of a material which has elastic properties similar to those of the inner liner. Suitable materials may include polyurethane, polyethylene (pebax), polyamide (nylon), and the like.

According to various embodiments, the sheath 904 may include a hemostasis valve 910 secured to a proximal end of the sheath 904. The hemostasis valve 910 may be comprised of a housing that defines axially aligned inlet and outlet ports, respectively for receiving the positioning mechanism 902, a guide catheter, or another elongate device therethrough. The hemostasis valve 910 may further include a structure for sealing against pressure through the inlet port when the positioning mechanism 902 or other device is not disposed in the hemostasis valve 910. In certain embodiments, an infusion tube 912 may also be mounted on the hemostasis valve 910.

As used herein, a coil electrode may be a helically wound element, filament, or strand. The filament forming the coil may have a generally round or a generally flat (e.g. rectangular) cross-sectional shape, as desired. However, other cross-sectional shapes may be used. The coil electrode may have a closed pitch, or in other words, adjacent windings may contact one another. Alternatively, the coil electrode may have an open pitch such that adjacent windings are spaced a distance from one another. The pitch may be uniform or varied along a length of the coil electrode. A varied pitch may be gradual tapered changes in pitch or abrupt or step-wise changes in pitch.

A coil electrode may have a length L that is generally larger than a width W. Round, oval or flattened coil electrodes may be used. Coil electrodes may have a length in the range of one to ten centimeters. In an example, a coil having a six or eight centimeter length may be used. In another example, a lead may have two four centimeter coils. Coils and leads may be in the range of four to ten French, or larger or smaller, in outer profile.

Coils and leads may be coated. For example, a thin permeable membrane may be positioned over a shock coil or other electrode and/or other portions of the lead to inhibit or to promote tissue ingrowth. Coatings, such as, but not limited to expanded polytetrafluoroethylene (ePTFE) may also be applied to the coil and/or lead to facilitate extraction and/or to reduce tissue ingrowth. In some embodiments, one or more of the electrodes, whether coils, rings, or segmented electrodes, include a high capacitive coating such as, but not limited to iridium oxide (IrOx), titanium nitride (TiN), or other "fractal" coatings which may be used, for example, to improve electrical performance. Steroidal and antimicrobial coatings may be provided as well.

The various components of the devices/systems disclosed herein may include a metal, metal alloy, polymer, a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers for use in the leads discussed above may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like.

In at least some embodiments, portions or all of the accessory devices and their related components may be doped with, made of, or otherwise include a radiopaque material. Radiopaque materials are understood to be materials capable of producing a relatively bright image on a fluoroscopy screen or another imaging technique during a medical procedure. This relatively bright image aids the user of the accessory devices and their related components in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the accessory devices and their related components to achieve the same result.

Any guidewire, introducer sheath, and/or guide catheter design suitable for medical interventions may be used for accessing the venous structures discussed herein.

The implantable systems shown above may include an implantable pulse generator (IPG) adapted for use in a cardiac therapy system. The IPG may include a hermetically sealed canister that houses the operational circuitry of the system. The operational circuitry may include various elements such as a battery, and one or more of low-power and high-power circuitry. Low-power circuitry may be used for sensing cardiac signals including filtering, amplifying and digitizing sensed data. Low-power circuitry may also be used for certain cardiac therapy outputs such as pacing output, as well as an annunciator, such as a beeper or buzzer, telemetry circuitry for RF, conducted or inductive communication (or, alternatively, infrared, sonic and/or cellular) for use with a non-implanted programmer or communicator. The operational circuitry may also comprise memory and logic circuitry that will typically couple with one another via a control module which may include a controller or processor. High power circuitry such as high power capacitors, a charger, and an output circuit such as an H-bridge having high power switches may also be provided for delivering, for example, defibrillation therapy. Other circuitry and actuators may be included such as an accelerometer or thermistor to detected changes in patient position or temperature for various purposes, output actuators for delivering a therapeutic substance such as a drug, insulin or insulin replacement, for example.

Some illustrative examples for hardware, leads and the like for implantable defibrillators may be found in commercially available systems such as the Boston Scientific Teligen™ ICD and Emblem S-ICD™ System, Medtronic Concerto™ and Virtuoso™ systems, and St. Jude Medical Promote™ RF and Current™ RF systems, as well as the leads provided for use with such systems.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of implanting a lead for use in a cardiac stimulus system in a patient, the method comprising:
    establishing access to a brachiocephalic vein of the patient;
    advancing a positioning mechanism from the brachiocephalic vein to and into an internal thoracic vein (ITV), wherein the positioning mechanism has a proximal end and a distal end, and the advancing step comprises advancing the distal end of the positioning mechanism into the ITV;
    obtaining a location of the positioning mechanism in the ITV;
    establishing an external access to the positioning mechanism at a position either in the ITV, the musculophrenic vein, or in the superior epigastric vein;
    attaching the lead to the positioning mechanism; and
    drawing the lead into the ITV by pulling on the positioning mechanism.

2. The method of claim 1 wherein the lead has a proximal end configured for attachment to an implantable pulse generator, and a distal end having one or more electrodes associated therewith; the step of attaching the lead to the positioning mechanism comprises attaching the distal end of the lead to the distal end of the positioning mechanism, and the step of drawing the lead into the ITV is performed by pulling on the proximal end of the positioning mechanism.

3. The method of claim 1 wherein the lead has a proximal end configured for attachment to an implantable pulse generator, and a distal end having one or more electrodes associated therewith; the step of attaching the lead to the positioning mechanism comprises attaching the proximal end of the lead to the proximal end of the positioning mechanism, and the step of drawing the lead into the ITV is performed by pulling on the distal end of the positioning mechanism at the location of the external access.

4. The method of claim 1 wherein the positioning mechanism is a guidewire.

5. The method of claim 1 wherein the distal end of the positioning mechanism has a shape controllable from the proximal end of the positioning mechanism.

6. The method of claim 1 wherein the distal end of the positioning mechanism includes an eyelet or suture hole.

7. The method of claim 1 wherein the lead has a distal end having a suture hole, and attaching the lead to the positing mechanism comprises using a suture to removeably secure the suture hole of the lead to the positioning mechanism.

8. The method of claim 1 wherein the distal end of the positioning mechanism includes a hook.

9. The method of claim 1 wherein establishing access to the brachiocephalic vein comprises accessing the subclavian vein and advancing the positioning mechanism from the access to the subclavian vein to the brachiocephalic vein.

10. The method of claim 1 wherein the step of obtaining a location of the positioning mechanism in the ITV further comprises obtaining a visualization of the positioning mechanism.

11. A method of implanting a lead for use in a cardiac stimulus system in a patient, the method comprising:
    establishing access to a brachiocephalic vein of the patient;
    advancing a positioning mechanism from the brachiocephalic vein to and into an internal thoracic vein (ITV), wherein the positioning mechanism has a proximal end and a distal end, and the advancing step comprises advancing the distal end of the positioning mechanism into the ITV;
    advancing the distal end of the positioning mechanism from the ITV to and into a tributary vein of the ITV;
    obtaining a visualization of the positioning mechanism in at least the tributary vein of the ITV;
    establishing an external access to the positioning mechanism at a position in the tributary vein of the ITV;
    attaching the lead to the positioning mechanism; and
    drawing the lead into at least the ITV by pulling on the positioning mechanism.

12. The method of claim 11 wherein the lead has a proximal end configured for attachment to an implantable pulse generator, and a distal end having one or more electrodes associated therewith; the step of attaching the lead to the positioning mechanism comprises attaching the distal end of the lead to the distal end of the positioning mechanism, and the step of drawing the lead into the ITV is performed by pulling on the proximal end of the positioning mechanism.

13. The method of claim 11 wherein the lead has a proximal end configured for attachment to an implantable pulse generator, and a distal end having one or more electrodes associated therewith; the step of attaching the lead to the positioning mechanism comprises attaching the proximal end of the lead to the proximal end of the positioning mechanism, and the step of drawing the lead into the ITV is performed by pulling on the distal end of the positioning mechanism at the location of the external access.

14. The method of claim 11 wherein the positioning mechanism is a guidewire.

15. The method of claim 11 wherein the distal end of the positioning mechanism has a shape controllable from the proximal end of the positioning mechanism.

16. The method of claim 11 wherein the distal end of the positioning mechanism includes an eyelet or suture hole.

17. The method of claim 11 wherein the lead has a distal end having a suture hole, and attaching the lead to the positing mechanism comprises using a suture to removeably secure the suture hole of the lead to the positioning mechanism.

18. The method of claim 11 further comprising detaching the lead from the positioning mechanism using electromagnetic (EM) energy to break a bond or link between the lead and the positioning mechanism.

\* \* \* \* \*